(12) United States Patent
Sasaki et al.

(10) Patent No.: US 9,145,360 B2
(45) Date of Patent: Sep. 29, 2015

(54) BRONSTED ACID COMPOUND, MANUFACTURING METHOD OF CONDENSATION COMPOUND, DISPERSION LIQUID OF CONDENSATION COMPOUND PARTICLES, MANUFACTURING METHOD OF ELECTROSTATIC IMAGE DEVELOPING TONER, MANUFACTURING METHOD OF BINDER RESIN, BINDER RESIN, DISPERSION LIQUID OF RESIN PARTICLES, ELECTROSTATIC IMAGE DEVELOPING TONER, ELECTROSTATIC IMAGE DEVELOPER, AND IMAGE-FORMING METHOD

(75) Inventors: Yuki Sasaki, Kanagawa (JP); Hirotaka Matsuoka, Kanagawa (JP); Satoshi Hiraoka, Kanagawa (JP); Fumiaki Mera, Kanagawa (JP); Yasuo Matsumura, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 767 days.

(21) Appl. No.: 13/067,944

(22) Filed: Jul. 8, 2011

(65) Prior Publication Data
US 2011/0269066 A1 Nov. 3, 2011

Related U.S. Application Data

(62) Division of application No. 11/598,801, filed on Nov. 14, 2006, now Pat. No. 8,003,821.

(30) Foreign Application Priority Data

Jun. 8, 2006 (JP) ................... 2006-159561

(51) Int. Cl.
C08G 63/68 (2006.01)
C07C 309/06 (2006.01)
C07C 309/39 (2006.01)
G03G 9/087 (2006.01)

(52) U.S. Cl.
CPC .......... *C07C 309/39* (2013.01); *G03G 9/08755* (2013.01); *G03G 9/08795* (2013.01)

(58) Field of Classification Search
CPC .................. C07C 309/39; G03G 9/08755
See application file for complete search history.

(56) References Cited

U.S. PATENT DOCUMENTS

| 3,030,208 | A | * | 4/1962 | Schellenberg et al. ....... 430/325 |
| 5,231,222 | A | | 7/1993 | Papa et al. |
| 7,341,817 | B2 | * | 3/2008 | Wada et al. ................ 430/270.1 |
| 2003/0186150 | A1 | | 10/2003 | Kitani et al. |
| 2003/0203308 | A1 | * | 10/2003 | Mizutani et al. ........... 430/270.1 |

FOREIGN PATENT DOCUMENTS

| JP | A-5-194318 | 8/1993 |
| JP | A 10-120598 | 5/1998 |
| JP | A 11-313692 | 11/1999 |
| JP | A 2003-029410 | 1/2003 |
| JP | A 2003-055302 | 2/2003 |
| JP | A 2003-155271 | 5/2003 |
| JP | A 2003-306535 | 10/2003 |
| JP | A-2003-330227 | 11/2003 |
| JP | A-2004-189797 | 7/2004 |
| JP | A-2005-140987 | 6/2005 |

OTHER PUBLICATIONS

Zaragoza Dorwald, Side Reactions in Organic Synthesis, 2005, WILEY-VCH Verlag GmbH & Co. KGaA, Weinheim, Preface. p. IX.*

Feb. 14, 2012 Notification of Reasons for Refusal issued in Japanese Application No. 2006-159561 with English-language translation.

* cited by examiner

*Primary Examiner* — Paul A Zucker
(74) *Attorney, Agent, or Firm* — Oliff PLC

(57) ABSTRACT

Methods and compositions including a compound represented by formula (I):

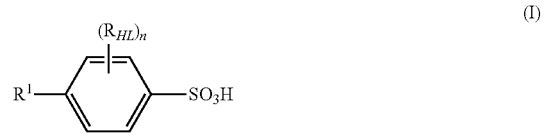

wherein n represents an integer of from 1 to 4, $R_{HL}$('s) each independently represents Cl or F, and $R^1$ represents an alkyl group having from 8 to 20 carbon atoms.

6 Claims, No Drawings

BRONSTED ACID COMPOUND, MANUFACTURING METHOD OF CONDENSATION COMPOUND, DISPERSION LIQUID OF CONDENSATION COMPOUND PARTICLES, MANUFACTURING METHOD OF ELECTROSTATIC IMAGE DEVELOPING TONER, MANUFACTURING METHOD OF BINDER RESIN, BINDER RESIN, DISPERSION LIQUID OF RESIN PARTICLES, ELECTROSTATIC IMAGE DEVELOPING TONER, ELECTROSTATIC IMAGE DEVELOPER, AND IMAGE-FORMING METHOD

This is a Division of application Ser. No. 11/598,801 filed Nov. 14, 2006, now U.S. Pat. No. 8,003,821 issued Aug. 23, 2011, which claims priority of Japanese Application No. 2006-159561 filed Jun. 8, 2006. The disclosure of the prior applications is hereby incorporated by reference herein in their entirety.

BACKGROUND

1. Technical Field

The present invention relates to a compound capable of improving, in particular, a surface activating property in alkylbenzenesulfonic; acids used as surfactants and Bronsted acids, and giving high reactivity as an acid catalyst even with a small amount at a low temperature.

The invention also relates to a manufacturing method of a condensation compound and a manufacturing method of a binder resin that are preferably used in development with a developer an electrostatic latent image formed by an electrophotography or an electrostatic recording method. The invention further relates to a dispersion liquid of condensation compound particles manufactured with the condensation compound and a dispersion liquid of resin particles manufactured with the binder resin, and an electrostatic image developing toner manufactured using these dispersion liquids. The invention still further relates to an electrostatic image developer with the electrostatic image developing toner, and an image-forming method.

2. Related Art

In recent years, with the rapid spread of digitized techniques, improvement of image quality is required in the output of printing and copying by users in general homes, offices and publishing fields. On the other hand, the requirements for lowering and saving energies are increasing for the activities of enterprises and the products resulted from the activities towards the realization of durable society. Accordingly, it becomes necessary to effectuate energy saving also in the fixing processes in the image-forming methods by electrophotography and electrostatic recording that consume great energies, and activities to lower the environmental load in the processes of manufacture of products with the materials. As the countermeasure to the former, a measure of lowering the fixing temperature of toners can be exemplified. By lowering the fixing temperature of toners, it is possible to shorten the waiting time until the fixable temperature of the surface of a fixing member at the input time of electric source, warming up time, in addition to energy saving, and lengthen the lifetime of fixing members.

As the binder resins of toners, vinyl polymers have been widely used so far, but vinyl polymers having a high molecular weight have a high softening point, so that it is necessary to set the temperature of a heat roller high to obtain fixed images having high glossiness, which is contradictory to the conservation of energy.

On the other hand, polyester resins are flexible as compared with vinyl polymers due to their stiff aromatic rings in the chains, and the molecular weight thereof can be set low when the mechanical strength is made equivalent. Further, since polyester resins have an advantage that they are easy in designing as resins for low temperature fixing in points of the entanglement of molecular chains and limiting molecular weight as compared with vinyl-based binder resins, polyesters are widely used as the binder resins for energy saving toners.

Polycondensation of polyester generally necessitates reaction of more than 10 hours under highly reduced pressure with stirring at high temperature exceeding 200° C. by huge power, so that accompanied by the consumption of large quantity of energy. Therefore, vast plant and equipment investments are required in many cases to obtain durability of reaction equipment.

SUMMARY

According to an aspect of the invention, there is provided a Brønsted acid that is a compound represented by formula (I):

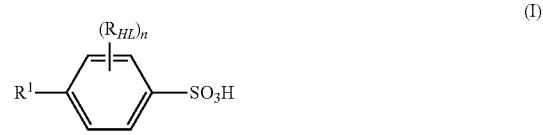

(I)

wherein n represents an integer of from 1 to 4, $R_{HL}$('s) each independently represents Cl or F, and $R^1$ represents an alkyl group having from 8 to 20 carbon atoms.

DETAILED DESCRIPTION

The Brønsted acid compound in the invention is a compound represented by formula (I):

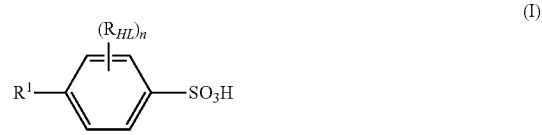

(I)

In formula (I), $R_{HL}$ represents Cl or F; $R^1$ represents an alkyl group having from 8 to 20 carbon atoms; and n represents an integer of from 1 to 4.

The present invention will be described in detail below.
Brønsted acid compound:

The Brønsted acid compound in the invention (hereinafter sometimes also referred to as merely "the compound of the invention") is a compound represented by formula (I), which is a compound having a surface activating property for having the hydrophobicity of the alkyl moiety.

By the electron attracting effect of a halogen atom, the compound of the invention becomes a stronger acid than an alkylbenzenesulfonic acid not substituted with a halogen atom. This fact results in the enhancement of catalytic effect in a reaction that necessitates an acid catalyst. As a result, the coloration and side reaction ascribable to the reduction of amount or the amount of an acid catalyst can be restrained.

As the surface activating property of the compound of the invention, hydrophobicity of the halide in addition to hydrophobicity of the alkyl moiety increase the surface activating property and, for example, stable micelles and oil droplets can be formed in emulsion polymerization. The effect of the invention is conspicuously revealed particularly in a dehydration reaction using an acid catalyst in an aqueous medium where the acid catalyst is used in combination with a surface activating property.

Accordingly, the compound in the invention can be preferably used as an acid catalyst in a dehydration reaction, and more preferably used as an acid catalyst in a dehydration reaction in an aqueous medium.

As the dehydration reaction, e.g., a dehydration reaction of a carboxylic acid and an alcohol, amine or thiol, and a polycondensation reaction of the later-described polycondensing monomers are preferably exemplified.

By using the compound of the invention as an acid catalyst and performing a condensation reaction or polycondensation reaction in an aqueous medium, a condensation compound or a polycondensation resin can be obtained in the state of a condensation compound particle dispersion liquid or polycondensation resin particle dispersion liquid that is dispersed in the aqueous medium, thus it is especially preferred in the usage of using a condensation compound or a polycondensation resin as particles or a particle dispersion liquid.

$R_{HL}$ in formula (I) represents a chlorine atom (Cl) or a fluorine atom (F) and is a substituent bonding on arbitrary position on the benzene ring.

$R_{HL}$ is preferably a fluorine atom from the aspect of reactivity. The bonding position of $R_{HL}$ is preferably the m-position, i.e., 3-position, to the sulfo group (the sulfo group is the 1-position) from the aspect of reactivity.

$R^1$ in formula (I) represents an alkyl group having from 8 to 20 carbon atoms that may be branched, the number of carbon atoms is preferably from 10 to 20, more preferably from 12 to 20.

In formula (I), when the number of carbon atoms of $R^1$ is smaller than the above range, there are cases where polycondensation does not sufficiently advance, the molecular weight does not increase, or the molecular weight distribution is widened attributable to the residual low molecular weight component. That the molecular weight is small, or the widening of molecular weight distribution attributable to a great amount of low molecular weight component is liable to result in hot offset at the time of fixing of a toner, or cause deterioration of powder fluidity of the toner, deterioration of preservation property under a high temperature condition, or deterioration of pulverization.

On the other hand, when the number of carbon atoms of $R^1$ is larger than the above range, stable manufacture of a catalyst is industrially difficult, and at the same time, there is the possibility that the catalytic function cannot be sufficiently exhibited due to low solubility.

The structure of alkyl group $R^1$ is not restricted, and the structure may be a straight-chain or branched structure. As the branched structure, any structure can be taken, such as a comb structure generally called a hard type, an ordinary bifurcated structure, or a cyclic structure of bonding two or more bifurcated structures. Of these structures, the structure of alkyl group $R^1$ is preferably a straight-chain structure.

Further, the number of carbon atoms of $R^1$ in the compound of the invention may be distributed, for example, it is sufficient that the maximum value of the number of carbon atoms of $R^1$ is from 8 to 20, and there is a case of including a catalyst having carbon atoms of 8 or less in the distribution of catalyst component. To have such distribution is the already known fact in the industry, and as the generally industrially allowable purity, it is preferred that the alkyl groups having from 8 to 20 carbon atoms account for 25 wt % or more of $R^1$. The separation and determination of the alkyl groups can be done with high performance liquid chromatography.

In formula (I), n that represents the substituents of $R_{HL}$ on the benzene ring is an integer of from 1 to 4, and n is preferably 1 or 2 in view of the balance of reactivity, and more preferably 1.

As the examples of the compounds represented by formula (I), 2-fluoro-4-octylbenzenesulfonic acid (o-fluoro-p-octylbenzenesulfonic acid), 3-fluoro-4-octylbenzenesulfonic acid (m-fluoro-p-octylbenzenesulfonic acid), 2-fluoro-4-decylbenzenesulfonic acid, 3-fluoro-4-decylbenzenesulfonic acid, 2-fluoro-4-dodecylbenzenesulfonic acid, 3-fluoro-4-dodecylbenzenesulfonic acid, 2-fluoro-4-pentadecylbenzenesulfonic acid, 3-fluoro-4-pentadecylbenzenesulfonic acid, 2-fluoro-4-octadecylbenzenesulfonic acid, 3-fluoro-4-octadecylbenzenesulfonic acid, 2-chloro-4-octylbenzenesulfonic acid, 3-chloro-4-octylbenzenesulfonic acid, 2-chloro-4-decylbenzenesulfonic acid, 3-chloro-4-decylbenzenesulfonic acid, 2-chloro-4-dodecylbenzenesulfonic acid, 3-chloro-4-dodecylbenzenesulfonic acid, 2-chloro-4-pentadecylbenzenesulfonic acid, 3-chloro-4-pentadecylbenzenesulfonic acid, 2-chloro-4-octadecylbenzenesulfonic acid, 3-chloro-4-octadecylbenzenesulfonic acid, 3,5-difluoro-4-octylbenzenesulfonic acid, 3,5-dichloro-4-octylbenzenesulfonic acid, 3-chloro-5-fluoro-4-octylbenzenesulfonic acid, 3,5-difluoro-4-decylbenzenesulfonic acid, 3,5-dichloro-4-decylbenzenesulfonic acid, 3-chloro-5-fluoro-4-decylbenzenesulfonic acid, 3,5-difluoro-4-dodecylbenzenesulfonic acid, 3,5-dichloro-4-dodecylbenzenesulfonic acid, 3-chloro-5-fluoro-4-dodecylbenzenesulfonic acid, 3,5-difluoro-4-pentadecylbenzenesulfonic acid, 3,5-dichloro-4-pentadecylbenzenesulfonic acid, and 3-chloro-5-fluoro-4-pentadecylbenzenesulfonic acid are preferably exemplified. In these structures, the alkyl moiety represented by $R^1$ can take any form such as a straight-chain, branched, or comb structure, but a straight-chain structure is more preferred.

Of the compounds represented by formula (I), as more preferred compounds, 2-fluoro-4-n-octylbenzenesulfonic acid, 3-fluoro-4-n-octylbenzenesulfonic acid, 2-fluoro-4-n-dodecylbenzenesulfonic acid, 3-fluoro-4-n-dodecylbenzenesulfonic acid, 2-fluoro-4-n-pentadecylbenzenesulfonic acid, 3-fluoro-4-n-pentadecylbenzenesulfonic acid, 2-fluoro-4-n-octadecylbenzenesulfonic acid, 3-fluoro-4-n-octadecylbenzenesulfonic acid, and 3,5-difluoro-4-dodecylbenzenesulfonic acid are exemplified.

Of these compounds, especially preferred compounds are 3-fluoro-4-n-dodecylbenzenesulfonic acid, 3-fluoro-4-n-pentadecylbenzenesulfonic acid and 3-fluoro-4-n-octadecylbenzenesulfonic acid.

The manufacturing method of the compound represented by formula (I) is not especially restricted, and any known methods can be used for the manufacture, or commercially available products may be used.

As the manufacturing method of the compound represented by formula (I), for example, a method of reacting alkylbenzene with a salt compound of an acid that is halogenated with an electrophilic halogenating agent, e.g., metal halide or potassium fluorophosphate, to manufacture on the benzene ring alkylbenzene halide to which a halogen atom is introduced, and then sulfonating the product, and a method of reacting alkylbenzenesulfonic acid salt with the above halide to introduce a halogen element, and then return the product to a sulfonic acid are preferably exemplified.

As the electrophilic halogenating agents, well-known compounds can be used, and commercially available products can also be used. When the halogen atom to be introduced is a fluorine atom, as halogenating agents, hexafluorophosphoric acid metals, e.g., potassium hexafluorophosphate and sodium hexafluorophosphate, fluorine gas, and commercially available electrophilic fluorinating agents can be preferably used.

Aqueous Medium:

Dehydration reaction using the compound of the invention is preferably performed in an aqueous medium to conspicuously reveal the effect of the invention.

As the aqueous media that can be used in the invention, water, e.g., distilled water and ion exchange water, and alcohols, e.g., ethanol and methanol, are exemplified. Of these, ethanol and water are preferred, and distilled water and ion exchange water are especially preferred. These media may be used alone, or two or more kinds of aqueous media may be used in combination.

The aqueous medium may contain a water-miscible organic solvent. Acetone and acetic acid are exemplified as the examples of the water-miscible organic solvents.

Organic Solvent:

An organic solvent may be used in condensation reaction in the invention.

The specific examples of the organic solvents usable in the invention include hydrocarbon solvents, e.g., toluene, xylene, mesitylene, etc., halide solvents, e.g., chlorobenzene, bromobenzene, iodobenzene, dichlorobenzene, 1,1,2,2-tetrachloroethane, p-chlorotoluene, etc., ketone solvents, e.g., 3-hexanone, acetophenone, benzophenone, etc., ether solvents, e.g., dibutyl ether, anisole, phenetol, o-dimethoxybenzene, p-dimethoxybenzene, 3-methoxytoluene, dibenzyl ether, benzyl phenyl ether, methoxynaphthalene, tetrahydrofuran, etc., thioether solvents, e.g., phenyl sulfide, thioanisole, etc., ester solvents, e.g., ethyl acetate, butyl acetate, pentyl acetate, methyl benzoate, methyl phthalate, ethyl phthalate, cellosolve acetate, etc., diphenyl solvents such as diphenyl ether, alkyl-substituted diphenyl ether, e.g., 4-methylphenyl ether, 3-methylphenyl ether, 3-phenoxytoluene, etc., halogen-substituted diphenyl ether, e.g., 4-bromophenyl ether, 4-chlorophenyl ether, 4-bromodiphenyl ether, 4-methyl-4'-bromodiphenyl ether, etc., alkoxy-substituted diphenyl ether, e.g., 4-methoxydiphenyl ether, 4-methoxyphenyl ether, 3-methoxyphenyl ether, 4-methyl-4'-methoxydiphenyl ether, etc., and cyclic diphenyl ether, e.g., dibrnzofuran, xanthene, etc., and these organic solvents may be used as mixture. As solvents, those capable of easily separating and isolating from water are preferred, and in particular for obtaining polyesters having a high average molecular weight, ester solvents, ether solvents and diphenyl ether solvents are more preferred, and alkylaryl ether solvents and ester solvents are especially preferred.

Ordinarily used polycondensing catalysts, e.g., metal catalyst, hydrolase, etc., can be used in combination with the compound of the invention.

As the metal catalysts, the following compounds can be exemplified, but the invention is by no means restricted thereto. For example, organic tin compounds, organic titanium compounds, organic tin halide compounds, and rare earth metal catalysts are exemplified.

As the organic tin compounds, organic titanium compounds, and organic tin halide compounds, those known as polycondensing catalysts can be used.

As the catalysts containing rare earth metals, catalysts containing scandium (Sc), yttrium (Y), lanthanoid, lanthanum as element (La), cerium (Ce), Praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), or lutetium (Lu) are effective, and alkylbenzenesulfonate, alkylsulfate, and those having a triflate structure are especially effective.

As the catalysts containing rare earth metals, those having a triflate structure such as scandium triflate, yttrium triflate, and lanthanoid triflate are preferred. Lanthanoid triflate is described in detail in Yuki Gosei Kagaku Kyokai-shi (Journal of The Institute of Organic Synthesis Chemistry), Vol. 53, No. 5, pp. 44-54. As the triflate, structural formula $X(OSO_2CF_3)_3$ is exemplified. Here, X represents rare earth metal, and it is more preferred that X represent scandium (Sc), yttrium (Y), ytterbium (Yb) or samarium (Sm).

A metal catalyst is used as a catalyst, the content of the metal derived from the catalyst in a resin to be obtained is preferably 100 ppm or less, more preferably 75 ppm or less, and still more preferably 50 ppm or less.

The usable hydrolases are not especially restricted so long as they are capable of catalyzing an ester synthesizing reaction. As the hydrolases, hydrolases belonging to group EC (enzyme No.) 3.1 (refer to Maruo and Tamiya compiled, Kohso Handbook (Enzyme Handbook), Asakura Shoten (1982)), e.g., carboxy esterase, lipase, phospholipase, acetyl esterase, pectin esterase, cholesterol esterase, tannase, monoacyl glycerol lipase, lactonase, lipoprotein lipase, etc., hydrolases belonging to group EC 3.2 acting on glycosyl compounds, e.g., esterase, glucosidase, galactosidase, glucuronidase, xylosidase, etc., hydrolases belonging to group EC 3.3, e.g., epoxide hydrase, etc., hydrolases belonging to group EC 3.4, e.g., aminopeptidase, chymotrypsin, trypsin, plasmin, subtilysin, etc., and hydrolases belonging to group EC 3.7, e.g., phloretin hydrase, etc., can be exemplified.

Of these esterases, enzymes that hydrolyzes and isolates fatty acids are especially called lipases, and lipases have advantages that stability in an organic solvent is high, catalyzing ability of ester synthesizing reaction shows high yield, and inexpensively available. Accordingly, it is also preferred to use lipases in the manufacturing method of polyesters in the invention in view of the yield and economy.

Lipases of various origins can be used, and as preferred ones, lipases capable of obtaining from microorganisms such as *Pseudomonas* genus, *Alcaligenes* genus, *Achromobacter* genus, *Candida* genus, *Aspergillus* genus, *Rhizopus* genus, *Mucor* genus, genus, lipases capable of obtaining from the seeds of plants, lipases capable of obtaining from animal tissues, and further, pancreatin, steapsin, etc., can be exemplified. Of these lipases, it is preferred to use lipases originating in microorganisms such as *Pseudomonas* genus, *Candida* genus and *Aspergillus* genus.

As basic catalysts, generally used organic basic compounds, nitrogen-containing basic compounds, and tetraalkyl- or arylphosphonium hydroxide such as tetrabutylphosphonium hydroxide are exemplified, but the invention is not restricted thereto.

As the organic basic compounds, ammonium hydroxides, e.g., tetramethylammonium hydroxide and tetraethylammonium hydroxide, as the nitrogen-containing basic compounds, amines, e.g., triethylamine, dibenzylmethylamine, pyridine, methylpyridine, methoxypyridine, quinoline, and imidazole, in addition, alkali metals, e.g., sodium, potassium, lithium, and cesium, hydroxide, hydride, and amide of alkaline earth metals, e.g., calcium, magnesium, and barium, bases of alkaline earth metals and acid, e.g., carbonate, phosphate, borate, and carboxylate, and bases with phenolic hydroxyl group are exemplified.

Further, compounds with alcoholic hydroxyl groups, and chelating compounds with acetylacetone can be exemplified, but the invention is not restricted thereto.

Condensation Compound and Manufacturing Method of the Same:

The manufacturing method of the condensation compounds of the invention includes a process of condensing a condensing composition with a Brønsted acid as a catalyst (hereinafter referred to as also "a condensing process").

The manufacturing method of a condensation compound of the invention can be preferably used as the manufacturing method of a releaser, and more preferably used as the manufacturing method of the releaser for an electrostatic image developing toner.

The condensation compound of the invention is a condensation compound manufactured by the above method.

The amount of the compound of the invention used in the manufacturing method of a condensation compound of the invention is preferably from 0.001 to 2 wt % based on the total weight of the condensable composition, and more preferably from 0.002 to 1 wt %. When the used amount is within the above range, reactivity is improved, the reaction at a low temperature can sufficiently advance and advantageous in the costs.

As the condensation compounds, an ester compound, an amide compound and a thioester compound are preferably exemplified.

The condensing compositions are not especially restricted so long as they are compounds or the combination of compounds capable of obtaining a condensation compound by using the compound of the invention, and compounds or the combination of compounds selected from the group consisting of a carboxylic acid compound, polyvalent carboxylic acid, alcohols, polyhydric alcohol, an amine compound, polyvalent amine, thiols, and polyvalent thiol are exemplified, and combinations of carboxylic acid with alcohols, polyhydric alcohol, an amine compound, polyvalent amine, thiols and/or polyvalent thiol, and combinations of polyvalent carboxylic acid with alcohols, an amine compound and/or thiols are preferably exemplified.

When the condensation compound in the invention is used as a releaser (in particular, a releaser for an electrostatic image developing toner), the condensation compound is preferably a condensation compound obtained by condensation in an aqueous medium, preferably an ester compound, and more preferably an ester compound obtained by condensation of a carboxylic acid compound and a polyhydric alcohol.

When the condensation compound in the invention is used as a releaser (in particular, a releaser for an electrostatic image developing toner), the melting point of the condensation compound of the invention is preferably from 60 to 130° C., more preferably from 70 to 110° C., and still more preferably from 80 to 100° C. When the melting point is in the above range, the balance of compatibility and dispersibility of the binder resin and the releaser is easily taken, and so preferred. When the melting point is 60° C. or higher, appropriate compatibility and preservation stability of the toner can be ensured, and when the melting point is 130° C. or lower, the condensation compound exudes at an appropriate temperature, so that good releasing property can be obtained.

The condensation reaction in the condensing process may be performed in an aqueous medium, in bulk, or in a solution, but to be performed in an aqueous medium is preferred to conspicuously exhibit the effect of the compound of the invention. Further, ordinary reaction conditions such as reaction under atmospheric pressure, under reduced pressure, under nitrogen current, etc., can be widely used in the condensation reaction.

In the condensation reaction in the condensing process, the above aqueous media and organic solvents can be preferably used.

Dispersion Liquid of Condensation Compound Particles:

The dispersion liquid of condensation compound particles in the invention (hereinafter also referred to as "condensation compound particle dispersion liquid") is a dispersion liquid of resin particles including at least particles containing the condensation compound dispersed in a dispersion medium, and the condensation compound contains the condensation compound manufactured by the manufacturing method of a condensation compound of the invention.

The condensation compound particle dispersion liquid of the invention can be preferably used as a dispersion liquid of releaser particles for electrostatic image developing toner.

In the invention, the dispersion medium of the condensation compound particle dispersion liquid is preferably an aqueous medium.

The median size (middle size) of the condensation compound particle dispersion liquid of the invention is preferably from 0.05 to 2.0 µm, more preferably from 0.1 to 1.5 µm, and still more preferably from 0.1 to 1.0 µm. When the median size is in the above range, the state of dispersion liquid of particles is stabilized, so that preferred. When condensation, compound particles having such a median size are used in the manufacture of a toner, the control of the particle size is easy, and excellent properties such as a releasing property and offset prevention at the time of fixation are preferably secured.

The median size of the condensation compound particles can be measured, for example, with a laser diffraction type particle size distribution measuring apparatus (LA-920, a product of Horiba, Ltd.).

The standard deviation of the condensation compound particles in the condensation compound particle dispersion liquid of the invention is preferably 0.40 or less, more preferably less than 0.30, and still more preferably 0.25 or less. When the standard deviation is in the above range, the particle size distribution does not widen, the releaser is properly and uniformly contained in the resin in the manufacture of a toner, and fixing ability, aggregation, toner particle size by the influence of coarse powder, particle size distribution, shape control, and powder fluidity are good and preferred. Further, the toner manufactured by using the condensation compound particle dispersion liquid of the invention is not accompanied by fogging, image deterioration and the deterioration of transfer efficiency, so that very preferred. The standard deviation can be computed with a laser diffraction type particle size distribution measuring apparatus (LA-920, a product of Horiba, Ltd.).

The condensation compound particle dispersion liquid of the invention can be manufactured by known methods with the condensation compound manufactured according to the manufacturing method of the invention.

As the manufacturing method of the condensation compound particle dispersion liquid of the invention, for instance, a method including a process of dispersing a material containing a condensation compound in an aqueous medium to obtain a condensation compound particle dispersion liquid can be exemplified.

In the dispersing process, for the purpose of increasing dispersing efficiency and improving stabilization of the condensation compound particle dispersion liquid, dispersing can be performed by adding a surfactant.

For dispersing a condensation compound in an aqueous medium and making particles, for example, a method of emulsifying and dispersing in an aqueous medium can be exemplified.

Further, in the manufacturing method of the condensation compound and the manufacturing method of the condensation compound particle dispersion liquid of the invention, in the case of performing emulsion condensation in an aqueous medium, the temperature of emulsification is preferably lower considering saving energy, forming speed of the condensation compound, and the thermal decomposition speed of the formed condensation compound, preferably from 40 to 150° C., and more preferably from 60 to 130° C. When the temperature of emulsification is 150° C. or lower, the necessary energy is not excessive, and the decomposition of the condensation compound due to high temperature does not occur and preferred, and when 40° C. or higher, the viscosity of the condensation compound becomes proper and particles can be made easily, so that preferred.

There are cases where condensation compound particles are classified for the purpose of controlling the particle size distribution of a toner. The classification has the effect of increasing the fixing property of the toner and image quality by excluding particles having inappropriate sizes.

Binder Resin and Manufacturing Method of the Same:

The manufacturing method of a binder resin of the invention includes a process of polycondensing a polycondensing monomer with the Brønsted acid compound of the invention as a catalyst (hereinafter also referred to as "a polycondensing process").

The manufacturing method of a binder resin of the invention can be more preferably used as the manufacturing method of the binder for an electrostatic image developing toner.

The binder resin of the invention is a binder resin manufactured by the above manufacturing method.

The amount of the compound of the invention used in the manufacturing method of the binder resin of the invention is preferably from 0.001 to 2 wt % based on the total weight of the polycondensing monomer, and more preferably from 0.002 to 1 wt %. When the used amount is within the above range, reactivity is improved, the reaction at a low temperature can sufficiently advance and advantageous in the costs.

The binder resin of the invention is preferably hardly colored by using the Brønsted acid compound of the invention as the catalyst.

The binder resin of the invention is not especially restricted so long as it is a resin obtained by polycondensing a polycondensing monomer with the Brønsted acid compound of the invention as a catalyst, but polyester is preferably used.

Polycondensing monomers usable in the invention are not especially restricted, and monomers capable of forming a crystalline polymer and amorphous polymers can be used, and monomers capable of forming amorphous polymers are preferably used.

As the polycondensing monomers, e.g., aliphatic, alicyclic, aromatic polyvalent carboxylic acids and alkyl esters thereof, polyhydric alcohols and ester compounds thereof, hydroxycarboxylic acid compounds, and polyhydric amine are exemplified, and polycondensation resins can be obtained by the direct esterification reaction and ester exchange reaction of the above polycondensing monomers.

Polyhydric alcohols are compounds having two or more hydroxyl groups in one molecule. The polyhydric alcohols are not especially restricted and the following monomers can be exemplified.

Diols are compounds having two hydroxyl groups in one molecule, e.g., propanediol, butanediol, pentanediol, hexanediol, heptanediol, octanediol, nonanediol, decanediol, dodecanediol, tetradecanediol, octadecanediol, etc., are exemplified.

As polyvalent ols other than diol, e.g., glycol, pentaerythritol, hexamethylolmelamine, hexaethylolmelamine, tetramethylolbenzoguanamine, tetraethylolbenzoguanamine, etc., are exemplified.

As polyhydric alcohols having a cyclic structure, the following monomers, e.g., cyclohexanediol, cyclohexanedimethanol, bisphenol A, bisphenol C, bisphenol E, bisphenol F, bisphenol P, bisphenol S, bisphenol Z, hydrogenated bisphenol, bisphenol, naphthalenediol, 1,3-adamantanediol, 1,3-adamantanedimethanol, 1,3-adamantanediethanol, hydroxy-phenylcyclohexane, etc., are exemplified, but the invention is not restricted thereto. In the invention, it is preferred for these bisphenols to have at least one alkylene oxide group. As the alkylene oxide groups, an ethylene oxide group, a propylene oxide group, a butylene oxide group, etc., are exemplified, but the invention is not restricted thereto. Ethylene oxide and propylene oxide are preferred, and the addition mol number is preferably from 1 to 3. When the addition mol number is in this range, the viscoelasticity and glass transition temperature of the polyester manufactured can be controlled appropriately for use as toner.

Of the above monomers, hexanediol, cyclohexanediol, octanediol, decanediol, dodecanediol, and alkylene oxide adducts of bisphenol A, bisphenol C, bisphenol E, bisphenol S, and bisphenol Z are preferably used.

Polyvalent carboxylic acids that can be used as polycondensing monomers are compounds having two or more carboxyl groups in one molecule. Of polyvalent carboxylic acids, dicarboxylic acids are compounds having two carboxyl groups in one molecule, and the examples include oxalic acid, succinic acid, fumaric acid, maleic acid, adipic acid, p-methyladipic acid, malic acid, malonic acid, pimelic acid, tartaric acid, azelaic acid, pimelic acid, sebacic acid, nonanedicarboxylic acid, decanedicarboxylic acid, undecanedicarboxylic acid, dodecanedicarboxylic acid, citraconic acid, cyclohexane-3,5-diene-1,2-carboxylic acid, citric acid, hexahydroterephthalic acid, mucic acid, phthalic acid, isophthalic acid, terephthalic acid, tetrachlorophthalic acid, chlorophthalic acid, nitrophthalic acid, p-carboxyphenylacetic acid, p-phenylenediacetic acid, m-phenylenediacetic acid, p-phenylenedipropionic acid, m-phenylenedipropionic acid, m-phenylenediglycolic acid, p-phenylenediglycolic acid, o-phenylenediglycolic acid, diphenylacetic acid, diphenyl-p,p'-dicarboxylic acid, 1,1-cyclopentenedicarboxylic acid, 1,4-cyclohexanedicarboxylic acid, 1,3-cyclohexanedicarboxylic acid, 1,2-cyclohexanedicarboxylic acid, 1,2-cyclohexenedicarboxylic acid, norbornene-2,3-dicarboxylic acid, 1,3-adamantanedicarboxylic acid, 1,3-adamantanediacetic acid, naphthalene-1,4-dicarboxylic acid, naphthalene-1,5-dicarboxylic acid, naphthalene-2,6-dicarboxylic acid, anthracenedicarboxylic acid, etc.

As polyvalent carboxylic acids other than dicarboxylic acids, for example, trimellitic acid, pyromellitic acid, naphthalenetricarboxylic acid, naphthalenetetracarboxylic acid, pyrenetricarboxylic acid, pyrenetetracarboxylic acid, etc., are exemplified.

These carboxylic acids may have a functional group other than a carboxyl group, and carboxylic acid derivatives, e.g., acid anhydrides and acid esters can also be used.

Of these polyvalent carboxylic acids, monomers that are preferably used are sebacic acid, nonanedicarboxylic acid, decanedicarboxylic acid, undecanedicarboxylic acid, dodecanedicarboxylic acid, p-phenylenediacetic acid, m-phenylenediacetic acid, p-phenylenedipropionic acid, m-phenylenedipropionic acid, 1,4-cyclohexanedicarboxylic acid, 1,3-cyclohexanedicarboxylic acid, naphthalene-1,4-dicarboxylic acid, naphthalene-1,5-dicarboxylic acid, naphthalene-2,6-dicarboxylic acid, trimellitic acid, and pyromellitic acid.

It is also possible to perform polycondensation with hydroxycarboxylic acid compounds having a carboxylic acid and a hydroxyl group in one molecule. For example, hydroxyoctanoic acid, hydroxynonanoic acid, hydroxydecanoic acid, hydroxyundecanoic acid, hydroxydodecanoic acid, hydroxytetradecanoic acid, hydroxytridecanoic acid, hydroxyhexadecanoic acid, hydroxypentadecanoic acid, hydroxystearic acid, etc., are exemplified as such compounds, but the invention is not restricted thereto.

In the invention, as polyvalent amines that can be used for obtaining polyamides, ethylenediamine, diethylenediamine, 1,2-propanediamine, 1,3-propanediamine, 1,4-butanediamine, 1,4-butenediamine, 2,2-dimethyl-1,3-butanediamine, 1,5-pentanediamine, 1,6-hexanediamine, 1,4-cyclohexanediamine, 1,4-cyclohexanebis(methylamine), etc., are exemplified.

Any of the above exemplified monomers can be used in the invention with no limitation, but it is preferred that polyesters to be manufactured are amorphous. Amorphous polyesters have high hardness and high fluidity at ordinary temperature, and have characteristics very suitable for toners in the aspects of restraint of offset, low temperature fixing property, and high image quality. Crystalline polyesters primarily consisting of straight-chain monomers have a sharp melt property ascribable to crystallizability and, although they have good low temperature fixing property, they are inferior in powder fluidity and image strength, so that amorphous polyesters are superior to crystalline polyesters in the characteristics as the main component of the binder resins. The confirmation of an amorphous property can be judged by differential thermal analysis (DSC) of manufactured polyester from the presence of glass transition temperature and melting point.

Here, the glass transition point of amorphous resin means a value measured according to the method prescribed in ASTM D3418-82 (the DSC method).

Incidentally, "crystallizability" in the "crystalline polyester resins" shows to have clear endothermic peak not stepwise endothermic change in differential scanning calorimetry (DSC), and specifically means that the half value width of endothermic peak measured at temperature increasing speed of 10° C./min is within 6° C.

On the other hand, resins whose half value width of endothermic peak is higher than 6° C., or resins not showing clear endothermic peaks mean to be amorphous resins.

As the monomers consisting of amorphous polyesters, among the above exemplified monomers, as polyhydric alcohols, alkylene oxide adducts of bisphenol A, bisphenol C, bisphenol E, bisphenol S, and bisphenol Z are exemplified, as polyvalent carboxylic acids, p-phenylenediacetic acid, m-phenylene-diacetic acid, p-phenylenedipropionic acid, m-phenylene-dipropionic acid, 1,4-cyclohexanedicarboxylic acid, 1,3-cyclohexanedicarboxylic acid, naphthalene-1,4-dicarboxylic acid, naphthalene-1,5-dicarboxylic acid, naphthalene-2,6-dicarboxylic acid, trimellitic acid, and pyromellitic acid are exemplified.

The binder resin obtained by the manufacturing method of a binder resin of the invention is not especially restricted as to the structure, but preferably the binder resin is polyester, more preferably a resin in which 90% or more of the repeating units in the polyester has a structure of Unit-A, Unit-B and/or Unit-C, and still more preferably a resin in which 90% or more of the repeating units in the polyester has a structure of Unit-A or Unit B. With respect to these structures, for example, in the case of Unit-A, the structure represented by Unit-A may be contained in the resin one kind alone, or two or more kinds may be mixed, and this is the same as in each of the following Unit structures. These binder resins are preferably amorphous resins.

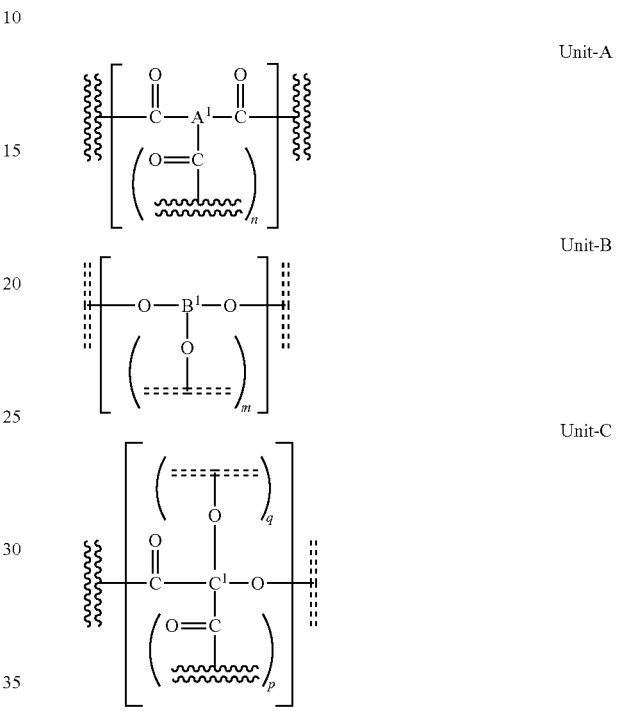

In Unit-A, $A^1$ represents a polyhydric hydrocarbon group that may contain a linking group, and n is the number of carboxyl bonding sites and represents an integer of 0 or more.

In Unit-B, $B^1$ represents a polyhydric hydrocarbon group that may contain a linking group and may be bonded to one or more alkylene oxide group(s), and m is the number of alkoxyl bonding sites and represents an integer of 0 or more.

In Unit-C, $C^1$ represents a polyhydric hydrocarbon group that may contain a linking group and may be bonded to one or more alkylene oxide group(s), p is the number of carboxyl bonding sites and represents an integer of 0 or more, and q is the number of alkoxyl bonding sites and represents an integer of 0 or more.

The double wavy line parts and double dotted line parts in Unit-A, to Unit-C represent that the places are the bonding sites to other structures. The double wavy line parts may be bonded to the double dotted line parts in Unit-B and the like and the structures other than Units-A to C and Units-D and E described later. The double dotted line parts may be bonded to the double wavy line parts and the structures other than Units-A to C and Units-D and E described later. The double wavy line parts are not bonded to each other and the double dotted line parts are not bonded to each other.

The above $A^1$ has preferably 3 or more carbon atoms, and $B^1$ has preferably 5 or more carbon atoms.

As the alkylene oxide group in $B^1$ and $C^1$, two or more alkylene oxide groups may be bonded, and in that case alkylene oxide groups of two or more kinds may be bonded. Further, it is preferred that alkylene oxide groups are directly bonded to the alkoxyl bonding site and the number is preferably the same at both ends of the alkoxyl site.

As the polyhydric hydrocarbon groups that may contain the linking group, alkane, alkene, alkyne, a group obtained by removing two or more hydrogen atoms from an aromatic hydrocarbon or hydrocarbon ring, a group obtained by bonding two or more of these groups, and a group obtained by bonding two or more of these groups and at least the bonding of a part is a linking group are exemplified.

The alkane, alkene and alkyne may be straight-chain or branched, and the carbon atom number of preferably from 1 to 20.

The aromatic hydrocarbon or hydrocarbon ring may further have an alkyl group, an alkenyl group and/or an alkynyl group on the cyclic structure, and the structure to which two or more rings are bonded may also be used. The number of carbon atoms of the aromatic hydrocarbon is preferably from 6 to 30. The number of carbon atoms of the hydrocarbon ring is preferably from 3 to 20, more preferably from 5 to 12, and still more preferably from 6 to 8.

As the above linking groups, —O—, —S—, —SO— and —SO$_2$— are preferably exemplified, and of these, —O— and —SO$_2$— are more preferred.

The above-described $B^1$ preferably has a bisphenol A structure (—C$_6$H$_4$—C(CH$_3$)$_2$—C$_6$H$_4$—), a bisphenol E structure (—C$_6$H$_4$—C(CH$_2$)—C$_6$H$_4$—), a bisphenol F structure (—C$_6$H$_4$—CH$_2$—C$_6$H$_4$—), a bisphenol P structure (—C(CH$_3$)$_2$-1,4-C$_6$H$_4$—C(CH$_3$)$_2$—), a bisphenol M structure (—C(CH$_3$)$_2$-1,3-C$_6$H$_4$—C(CH$_3$)$_2$—), a bisphenol S structure (—C$_6$H$_4$—SO$_2$—C$_6$H$_4$—), a bisphenol Z structure (—C$_6$H$_4$—C$_6$H$_{10}$—C$_6$H$_4$—), or a group obtained by bonding one or more alkylene oxide groups to any of the above groups, and more preferably —C$_6$H$_4$—C(CH$_3$)$_2$—C$_6$H$_4$—, —C$_6$H$_4$—SO$_2$—C$_6$H$_4$—, —C$_6$H$_4$—C$_6$H$_{10}$—C$_6$H$_4$—, or a group obtained by bonding one or more alkylene oxide groups to any of the above groups.

The number n at the carboxyl bonding site in Unit-A is preferably from 0 to 5, and more preferably from 0 to 2.

The number m at the alkoxyl bonding site in Unit-B is preferably from 0 to 5, and more preferably from 0 to 2.

The number p at the carboxyl bonding site in Unit-C is preferably from 0 to 5, and more preferably 0.

The number q at the alkoxyl bonding site in Unit-C is preferably from 0 to 5, and more preferably 0.

When n, m, p and q each represents 0, which means that the carboxyl bonding site or the alkoxyl bonding site in the parentheses does not exist, and when n, m, p and q each represents an integer of 1 or more, which means that the carboxyl bonding site or the alkoxyl bonding site in the parentheses exists in number of 1 or more integer.

As the binder resin obtained by the manufacturing method of a binder resin of the invention, a resin in which 90% or more of the repeating units in Units-A to C has the structure of Unit-AB is preferred.

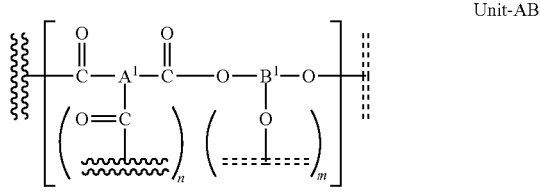

Unit-AB

In Unit-AB, $A^1$ represents a polyhydric hydrocarbon group that may contain a linking group, $B^1$ represents a polyhydric hydrocarbon group that may contain a linking group and may be bonded to one or more alkylene oxide group(s), n is the number of carboxyl bonding sites and represents an integer of 0 or more, and m is the number of alkoxyl bonding sites and represents an integer of 0 or more. The double wavy line parts and double dotted line parts represent that the places are the bonding sites to other structures. The double wavy line parts may be bonded to the double dotted line parts and the structures other than Units-A to E. The double dotted line parts may be bonded to the double wavy line parts and the structures other than Units-A to E. The double wavy line parts are not bonded to each other and the double dotted line parts are not bonded to each other.

$A^1$, $B^1$, n and m in Unit-AB are the same as $A^1$, $B^1$, n and m in Unit-A or B, and the preferred ranges are also the same.

Unit-A is preferably Unit-D.

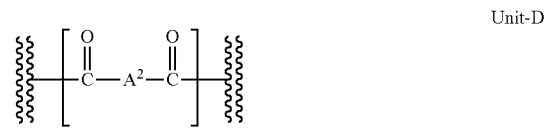

Unit-D

In Unit-D, $A^2$ represents alkane having from 1 to 20 carbon atoms, a group obtained by removing two or more hydrogen atoms from an aromatic hydrocarbon group having from 6 to 20 carbon atoms or a hydrocarbon ring having from 3 to 20 carbon atoms, or a group obtained by bonding two or more of this group.

The double wavy line parts in Unit-D represent that the places are the bonding sites to other structures. The double wavy line parts may be bonded to the double dotted line parts in Unit-B and the like and the structures other than Units-A to E. The double wavy line parts are not bonded to each other.

As $A^2$, a group having 3 or more carbon atoms is preferred, and more preferably a straight-chain alkylene group having from 6 to 18 carbon atoms, a phenylene group, a naphthylene group, a cyclohexylene group, a hydrocarbon ring containing crosslinking such as norbornene or adamantane, a group obtained by bonding two alkylene groups to a phenylene group (e.g., —CH$_2$—C$_6$H$_4$—CH$_2$— and —CH$_2$CH$_2$—C$_6$H$_4$—CH$_2$CH$_2$—), a group obtained by bonding two alkylene groups to a naphthylene group, and a group obtained by bonding two alkylene groups to a cyclohexylene group are exemplified.

Unit-B is preferably Unit-E.

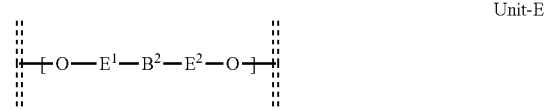

Unit-E

In Unit-E, $B^2$ represents a straight-chain alkylene group, a hydrocarbon ring, or a group obtained by removing two hydroxyl groups from a bisphenol compound, and $E^1$ and $E^2$ each represents a single bond, an alkylene oxide group, or a group obtained by bonding two or more alkylene oxide groups.

The double dotted line parts in Unit-E represent that the places are the bonding sites to other structures. The double dotted line parts may be bonded to the double wavy line parts in Unit-A and the like and the structures other than Units-A to E. The double dotted line parts are not bonded to each other.

As the bisphenol compound, bisphenol A, bisphenol E, bisphenol P, bisphenol M, bisphenol S and bisphenol Z are preferably exemplified.

When $B^2$ represents a straight-chain alkylene group, $E^1$ and $E^2$ each preferably represents hydrocarbon, and when $B^2$ represents a group obtained by removing two hydroxyl groups from a bisphenol compound, $E^1$ and $E^2$ each represents an alkylene oxide group, or a group obtained by bonding two or more alkylene oxide groups, the hydrocarbon ring may take every of the above. As the alkylene oxide group, an ethylene oxide group and/or a propylene oxide group are more preferred.

The binder resin of the invention is particularly preferably polyester in which 80% or more of the repeating units in the resin is Unit-D or Unit-E.

The binder resin of the invention is particularly preferably polyester in which 80% or more of the repeating units in the resin is Unit-DE.

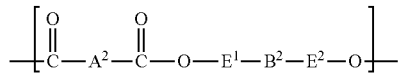

Unit-DE

In Unit-DE, $A^2$ represents alkane having from 1 to 20 carbon atoms, a group obtained by removing two or more hydrogen atoms from an aromatic hydrocarbon group having from 6 to 20 carbon atoms or a hydrocarbon ring having from 3 to 20 carbon atoms, or a group obtained by bonding two or more of this group, $B^2$ represents a straight-chain alkylene group, or a group obtained by removing two hydroxyl groups from a bisphenol compound, and $E^1$ and $E^2$ each represents a single bond, an alkylene oxide group, or a group obtained by bonding two or more alkylene oxide groups.

$A^2$, $B^2$, $E^1$ and $E^2$ in Unit-DE are the same as $A^2$, $B^2$, $E^1$ and $E^2$ in Unit-D or Unit-E, and the preferred ranges are also the same.

The glass transition temperature of the binder resin for electrostatic image developing toner manufactured in the invention is preferably from 30 to 80° C. in view of the fixing property and image-forming property. When the glass transition temperature is higher then 30° C., powder fluidity of the toner at ordinary temperature is good, excellent aggregating power of the binder resin itself is secured in a high temperature region, and hot offset hardly occurs in fixation, so that preferred. Further, when the glass transition temperature is lower than 80° C., sufficient melting can be obtained and the lowest fixing temperature is difficult to rise and preferred. The glass transition temperature is more preferably from 35 to 75° C., and most preferably from 45 to 65° C. Glass transition temperature can be controlled by the molecular weight of the binder resin, the constitution of the monomer of the binder resin, and the addition of a crosslinking agent.

The binder resin of the invention can be obtained at lower temperature than conventional reaction temperature, so that advantageous in energy costs. The reaction temperature is preferably 70° C. or more and less than 150° C., more preferably from 70 to 140° C., and still more preferably 80° C. or more and less than 140° C. When the reaction temperature is lower than this range, there are cases where the reduction of reactivity and the restraint of molecular weight extension attributable to the solubility of monomer and the decrease of the degree of catalytic activity occur, while when higher than the above range, it deviates from the original object of manufacturing method by low energy. Further, there is the possibility that coloration of the resin ascribable to high temperature or decomposition of the formed polycondensation resin occurs.

The polycondensation reaction in the polycondensing process can be performed by ordinary polycondensation methods such as polymerization in water, e.g., emulsion polymerization and suspension polymerization, and bulk polymerization, solution polymerization and interfacial polymerization, but polycondensation in water is preferably used. The reaction can be performed under atmospheric pressure, but it is the object to increase the molecular weight of the polycondensation resin, ordinary reaction conditions, such as reaction under reduced pressure or under nitrogen current, etc., can be widely used.

The polycondensation reaction in the polycondensing process can be performed with the above aqueous solvents or organic solvents.

Further, in the invention, for obtaining polyester having a high weight-average molecular weight, a dehydrating or monomer removing agent may be added to an organic solvent. As the specific examples of the monomer removing agents, molecular sieves, e.g., molecular sieve 3A, molecular sieve 4A, molecular sieve 5A, and molecular sieve 13X, alumina, silica gel, calcium chloride, calcium sulfate, diphosphorus pentoxide, concentrated sulfuric acid, magnesium perchlorate, barium oxide, calcium oxide, potassium hydroxide, sodium hydroxide, and metal hydrides, e.g., calcium hydride, sodium hydride, aluminum lithium hydride, etc., and alkali metal, e.g., sodium, etc., are exemplified. Of these monomer removing agents, molecular sieves are preferred for the easiness of handling and reclaiming.

For the binder resin manufactured by the manufacturing method of a binder resin of the invention to have aptitude as a toner, the weight-average molecular weight of the binder resin is preferably from 5,000 to 50,000, more preferably from 7,000 to 35,000, and still more preferably from 8,000 to 30,000. When the weight-average molecular weight is 5,000 or more, the powder fluidity at ordinary temperature is excellent, blocking of the toner is difficultly generated, aggregating property of the binder resin for toner is sufficient, and hot offset hardly occurs and to preferred. While when the weight-average molecular weight is 50,000 or less, hot offset resistance and the lowest fixing temperature are both good, the time required in polycondensation is short, and the temperature at the time of polycondensation is low, so that excellent manufacturing efficiency can be ensured.

The number-average molecular weight of the binder resin manufactured by the manufacturing method of a binder resin of the invention is preferably the range of from 1,000 to 10,000, more preferably from 1,500 to 8,000, and still more preferably from 1,800 to 7,000. The number-average molecular weight of the binder resin in the above range is preferred in view of the stability of the powder against heat.

Weight-average molecular weight and number-average molecular weight of the binder resin can be measured by known methods, for example, these can be measured according to gel permeation chromatography (GPC).

The molecular weight distribution of the binder resin in the invention is preferably the range of from 1.0 to 4.0, and more preferably from 1.0 to 3.5. In the above range of the molecular weight distribution, the fixing characteristics and the productivity of the toner are uniform and preferred.

It is possible to polycondensate amorphous polyesters that can be used in the invention with monomers other than described above so long as the characteristics are not impaired. For example, monovalent carboxylic acids, monovalent alcohols, and radical polymerizable monomers having unsaturated bond can be exemplified as such other monomers. For capping the terminals of polyesters, these monofunctional monomers can effectively modify the terminals and control the properties of polyesters. Monofunctional monomers may be used from the initial stage of polymerization or may be added halfway through polymerization.

In the invention, polymerization reaction of the above monomers and prepolymers manufactured in advance can be included as polycondensing process. The prepolymers are not restricted so long as they can be melted in or uniformly mixed with the monomers.

Further, the binder resins in the invention may contain a homopolymer of the above monomer, a copolymer of two or more monomers in combination including the above monomer, or mixture of these, a graft polymer, or a partially branched structure or a crosslinking structure.

Resin Particle Dispersion Liquid:

The resin particle dispersion liquid of the invention (hereinafter also referred to as "resin particle dispersion liquid") is a resin particle dispersion liquid including resin particles containing a binder resin having been dispersed in a dispersion medium, and the binder resin contains the binder resins obtained by the manufacturing method of a binder resin of the invention.

The resin particle dispersion liquid of the invention can be preferably used as the resin particle dispersion liquid for an electrostatic image developing toner.

In the invention, the dispersion medium of the resin particle dispersion liquid is preferably the above-described aqueous medium.

The median size (middle size) of the resin particle dispersion liquid of the invention is preferably from 0.05 to 2.0 µm, more preferably from 0.1 to 1.5 µm, and still more preferably from 0.1 to 1.0 µm. By bringing the median size into the above range, the dispersing state of the resin particles in the aqueous medium is stabilized and preferred. When resin particles having such a median size are used in the manufacture of a toner, the control of the particle size is easy, and excellent properties such as a releasing property and offset prevention at the time of fixation are preferably secured.

The median size of the resin particles can be measured, for example, with a laser diffraction type particle size distribution measuring apparatus (LA-920, a product of Horiba, Ltd.).

The standard deviation of the resin particles in the resin particle dispersion liquid is preferably 0.40 or less, more preferably less than 0.30, and still more preferably 0.25 or more. When the standard deviation of the resin particles in the resin particle dispersion liquid is in the above range, the particle size distribution of the resin particles does not widen, a releaser is appropriately and uniformly contained in the resin at the time of the manufacture of a toner, and good fixing property and aggregating property are obtained, the particle size of the toner is free from the influence of the coarse particles, and proper particle size distribution, shape controllability, and powder fluidity are ensured and preferred. Further, in the toner manufactured with the resin particle dispersion liquid of the invention, fogging, image degeneration and reduction of transfer efficiency do not occur and preferred. Standard deviation can be measured, for example, with a laser diffraction type particle size distribution measuring apparatus (LA-920, a product of Horiba, Ltd.).

The resin particle dispersion liquid can be manufactured with the binder resin manufactured by the manufacturing method of the invention according to known methods.

As the manufacturing method of the resin particle dispersion liquid, e.g., a method including a dispersing process of dispersing the material containing the binder resin in an aqueous medium to thereby obtain a resin particle dispersion liquid is exemplified.

In the dispersing process, for increasing dispersing efficiency and improving the stabilization of the resin particle dispersion liquid, it is preferred to perform dispersion by adding a surfactant.

As a method for dispersing the binder resin of the invention in an aqueous medium to make particles, for example, a suspension polymerization method in an aqueous medium, a dissolution suspension method, a mini-emulsion method, a micro-emulsion method, a multistage swelling method, or an emulsion polymerization method including seed polymerization can be used in the manufacture of the binder resin, as described above.

In the manufacturing method of the binder resin and the manufacturing method of a resin particle dispersion liquid of the invention, when emulsion polycondensation is performed in an aqueous medium, the emulsification temperature is preferably lower considering energy saving, growing speed of the polymer and thermal decomposition speed of the formed polymer, preferably from 40 to 150° C., and more preferably from 60 to 130° C. When the emulsification temperature is 150° C. or lower, the necessary energy is not excessive and the reduction of molecular weight ascribable to the decomposition of the resin due to high temperature is not generated, so that preferred, while when it is 40° C. or higher, proper resin viscosity is obtained and the resin is easily atomized, so that preferred.

A method for dispersing the binder resin in an aqueous medium to make particles can be selected from known methods, e.g., a forced emulsification method, a self emulsification method, and a phase reversal emulsification method. Of these methods, a self emulsification method and a phase reversal emulsification method are preferably used considering the energy required for emulsification, a controlling property of particle size of the obtained emulsion, and stability.

A self emulsification method and a phase reversal emulsification method are described in Cho-Biryushi Polymer no Oyo Gijutsu (Application Technology of Super Fine Polymers), CMC Publishing Co., Ltd. As the polar groups for use in a self emulsion method, a carboxyl group and a sulfon group can be used, but when applied to the amorphous polyester binder resin for toner, a carboxyl group is preferably used.

When an organic solvent is used in the dispersing process, at least a process of removing a part of the organic solvent, and a process of forming resin particles may be included in the manufacturing method of a resin particle dispersion liquid.

For example, after emulsifying a binder resin-containing material, it is preferred to solidify the emulsified solution by removing a part of the organic solvent. As the specific methods of solidification, a method of, after emulsion dispersing a polycondensation resin-containing material in an aqueous medium, feeding air or inert gas such as nitrogen while stirring the solution to dry the organic solvent at gas-liquid interface (an air blowing drying method), a method of carrying out drying with bubbling inert gas according to necessity while maintaining pressure reduction (a pressure reduction topping method), and a method of discharging, like shower, an emulsified dispersion liquid obtained by emulsifying and dispersing a polycondensation resin-containing material in an aqueous medium or an emulsified solution of a polycondensation resin-containing material, from pores to a saucer, and repeating this procedure to dry the organic solvent (a shower system desolvating method) are known. It is preferred to arbitrarily select and combine these methods in desolvation by the evaporating speed and the solubility in water of the organic solvent to be used.

There are cases where resin particles are classified for the purpose of controlling the particle size distribution of a toner. The exclusion of particles having unsuitable particle sizes by classification is effective to improve the fixing property of the toner and image quality.

Electrostatic Image Developing Toner and Manufacturing Method of the Same:

With the increasing requirements for higher quality in recent years, many chemical manufacturing methods of toners have been adopted as the countermeasure of manufacturing technique of making the particle size of toner smaller and with low energy. As chemical manufacturing method of toner using polyester in the invention, general purpose manufacturing methods can be used, but a aggregation coalescence method is preferred. The aggregation coalescence method is a known aggregating method of manufacturing latex of a binder resin dispersed in water, and aggregating (associating) the latex with other toner materials.

The manufacturing method of the electrostatic image developing toner (also referred to as merely "toner") of the invention is a manufacturing method of an electrostatic image developing toner including a process of obtaining aggregated particles by aggregating, in a dispersion liquid containing a condensation compound particle dispersion liquid or a resin particle dispersion liquid, the particles (hereinafter also referred to as "a aggregating process"), and a process of melting the aggregated particles by heating (hereinafter also referred to as "a melting process"), wherein the condensation compound particle dispersion liquid is the condensation compound particle dispersion liquid of the invention, and the resin particle dispersion liquid is the resin particle dispersion liquid of the invention.

In the manufacturing method of the toner of the invention, the condensation compound particle dispersion liquid of the invention can be used as a releaser particle dispersion liquid, and the resin particle dispersion liquid of the invention can be used as a binder resin dispersion liquid, and either one of the dispersion liquids or both may be used.

For example, it is possible to manufacture a toner that is controlled in particle size and particle size distribution by using a resin particle dispersion liquid, i.e., latex, according to a aggregating (associating) method. In detail, such a toner can be manufactured by mixing latex with a colorant particle dispersion liquid and a releaser particle dispersion liquid (the condensation compound particle dispersion liquid of the invention may be used as the releaser particle dispersion liquid), further adding a aggregating agent to generate hetero aggregation and form aggregated particles having the toner particle size, and then heating the aggregated particles at a temperature higher than the glass transition temperature or melting point of the resin particles to melt and coalesce the aggregated particles, washing, and drying. By selecting the heating temperature conditions, the shape of the toner can be controlled from amorphous to spherical according to the manufacturing method.

In the aggregating process, it is also possible to mix a resin particle dispersion liquid other than the resin particle dispersion liquid of the invention and the resin particle dispersion liquid of the invention and perform the processes on and after the aggregating process. At that time, multilayered particles can also be made by forming first aggregated particles by aggregating the resin particle dispersion liquid of the invention in advance, and then further adding thereto the resin particle dispersion liquid of the invention or other resin particle dispersion liquid. Multilayered particles can be made in reverse order.

Further, for example, in the aggregating process, after forming first aggregated particles by aggregating a resin particle dispersion liquid containing the binder resin of the invention and a colorant particle dispersion liquid in advance, and adding thereto the resin particle dispersion liquid containing the binder resin of the invention or other resin particle dispersion liquid to form a second shell layer on the first particle surface. In this exemplification, the colorant particle dispersion liquid is prepared separately but of course the colorant may be previously blended with the resin particles.

After terminating melting/coalescent process of aggregated particles, a desired toner is obtained through arbitrary washing process, solid liquid separating process and drying process, and considering electrification, it is preferred to perform displacement washing sufficiently with ion exchange water in the washing process. The solid liquid separating process is not especially restricted, but suction filtration and pressure filtration are preferred in view of productivity. Further, the drying process is also not particularly restricted, but in the light of productivity, freeze drying, flash jet drying, fluidized drying and vibrating type fluidized drying are preferably used.

As the aggregating agents, besides surfactants, inorganic salts and divalent or higher metallic salts can be preferably used. Metallic salts are particularly preferred in characteristics such as aggregation control and electrification of toner. Metallic salt compounds used in aggregation can be obtained by dissolving an ordinary inorganic metallic compound or a polymer of the compound in a resin particle dispersion liquid. Metallic elements constituting inorganic metallic salts have divalent or higher electrification belonging to groups 2A, 3A, 4A, 5A, 6A, 7A, 8, 1B, 2B and 3B of the periodic table (long form of the periodic table), and those dissolving in a resin particle aggregation system in the form of an ion are sufficient. As preferred inorganic metallic salts, inorganic metallic salts, e.g., calcium chloride, calcium nitrate, barium chloride, magnesium chloride, zinc chloride, aluminum chloride, aluminum sulfate, etc., and inorganic metallic salt polymers, e.g., polyalminum chloride, aluminum polyhydroxide, calcium polysulfide, etc., are exemplified, and aluminum salt and a polymer thereof are preferred of them. In general, for obtaining sharper particle size distribution, as to the valence of inorganic metallic salt, divalent is preferred to monovalent, trivalent or more is preferred to divalent, and even the same valence, a polymer type inorganic metallic salt is more suitable.

In the invention, if necessary, known additives can be mixed, and they can be used alone or two or more in combination, in the range not adversely affecting the result of the invention. As known additives, e.g., a flame retardant, an auxiliary flame retardant, a brightener, a waterproof agent, a water repellent, an inorganic filler (a surface improver), a releaser, an antioxidant, a plasticizer, a surfactant, a dispersant, a lubricant, a filler, an extender pigment, a binder, a static controller, etc., are exemplified. These additives can be blended any time in manufacturing a coating agent.

As the examples of inner additives, ordinarily used various static controller such as quaternary ammonium salt compounds and nigrosine compounds can be used, and from the point of the stability in manufacture and the reduction of contamination due to waste solutions, materials hardly soluble in water are preferred.

As the examples of releasers, besides the condensation compound of the invention, low molecular weight olefins, e.g., polyethylene, polypropylene, polybutene, etc., silicones having a softening point by heating, fatty acid amides, e.g., oleic acid amide, erucic acid amide, ricinoleic acid amide, stearic acid amide, etc., vegetable waxes, e.g., ester wax, carnauba wax, rice wax, candelilla wax, Japan wax, jojoba oil, etc., animal wax, e.g., beeswax, etc., mineral, petroleum waxes, e.g., montan wax, ozokerite, ceresin, paraffin wax, micro-crystalline wax, Fischer-Tropsch wax, etc., and modified products of these compounds can be used.

By dispersing these waxes with an ionic surfactant and high molecular weight electrolytes such as a high molecular weight acid or a high molecular weight base in water, and heating at temperature higher than the melting point while applying strong shear force with a homogenizer or a pressure discharge type disperser having high power to thereby make particles, a dispersion liquid of particles having a particle size of 1 μm or less can be manufactured.

As flame retardants and auxiliary flame retardants, already generally used bromine-based flame retardants, antimony trioxide, magnesium hydroxide, aluminum hydroxide, and ammonium polyphosphate can be exemplified, but the invention is not restricted to these compounds.

As the coloring components, carbon blacks, e.g., furnace black, channel black, acetylene black, thermal black, etc., inorganic pigments, e.g., red iron oxide, ultramarine, Prussian blue, titanium oxide, etc., azo pigments, e.g., Fast Yellow, disazo yellow, Pyrazolone Red, Chelate Red, Brilliant Carmine, para-brown, etc., phthalocyanine pigments, e.g., copper phthalocyanine, non-metal phthalocyanine, etc., and condensed polycyclic pigments, e.g., Flavanthrone Yellow, Dibromoanthrone Orange, Perylene Red, Quinacridone Red, Dioxazine Violet, etc., are exemplified. Further, various pigments are exemplified as shown below, and these pigments can be used alone, or two or more in combination, e.g., Chrome Yellow, Hansa Yellow, Benzidine Yellow, Durene Yellow, Quinoline Yellow, Permanent Orange GTR, Pyrazolone Orange, Vulcan Orange, Watchung Red, Permanent Red, Du Pont Oil Red, Lithol Red, Rhodamine B Lake, Lake Red C, Rose Bengal, Aniline Blue, Ultramarine, Chalco Oil Blue, Methylene Blue Chloride, Phthalocyanine Blue, Phthalocyanine Green, Malachite Green Oxalate, C.I. Pigment Red 48:1, C.I. Pigment Red 122, C.I. Pigment Red 57:1, C.I. Pigment Yellow 12, C.I. Pigment Yellow 97, C.I. Pigment Yellow 17, C.I. Pigment Blue 15:1, C.I. Pigment Blue 15:3, etc.

After drying similarly to ordinary toners, by adding inorganic particles e.g., silica, alumina, titania, or calcium carbonate, resin particles, e.g., vinyl resin, polyester or silicone in a dried state with applying shear force to the surface of the toner, the toner of the invention can also be used as a fluidizing assistant and a cleaning assistant.

The examples of surfactants usable in the invention include anionic surfactants, e.g., sulfates, sulfonates, phosphates, soap, etc., cationic surfactants, e.g., amine salt type, quaternary ammonium salt type, etc., and nonionic surfactants, e.g., polyethylene glycol, alkylphenol ethylene oxide adducts, polyhydric alcohols, etc., and to use these surfactants in combination is effective. As dispersing means, ordinary used machines such as a rotating shearing type homogenizer, or a ball mill, sand mill or Dyno mill having media can be used.

The volume-average particle diamter ($D_{50}$) of the toner of the invention is preferably from 3.0 to 20.0 μm, and more preferably from 3.0 to 9.0 μm. When $D_{50}$ is 3.0 μm or more, proper adhesion property and developability can be obtained and preferred. When $D_{50}$ is 20.0 μm or less, excellent resolution of image can be ensured. The volume-average particle size ($D_{50}$) of the toner can be measured with a laser diffraction type particle size distribution measuring apparatus and the like.

The volume-average particle distribution GSDv of the toner of the invention is preferably 1.4 or less, and more preferably 1.3 or less. As the particle distribution, by using cumulative distribution $D_{16}$ and $D_{84}$, the following volume-average particle distribution GSD or number GSD can be simply used.

$$\text{Volume } GSDv = (\text{volume } D_{84}/\text{volume } D_{16})^{0.5}$$

When GSDv is 1.4 or less, particle size becomes uniform, fixing property is excellent, accident of apparatus ascribable to fixing failure hardly occurs, and contamination in the apparatus due to splashing of the toner and deterioration of developer are difficult to occur, so that preferred. Volume-average particle distribution GSD can be measured with a laser diffraction type particle size distribution measuring apparatus and the like.

The shape factor SF1 of the toner of the invention is preferably from 100 to 140 from the point of image forming property, and more preferably from 110 to 135. At this time, SF1 is computed as follows.

$$SF1 = \frac{(ML)^2}{A} \times \frac{\pi}{4} \times 100$$

where ML is the absolute longest length of a particle, and A is the projected area of a particle.

These are made numerical values by taking in mainly a microscopic image or scanning electron microscopic image with a Ruzex image analyzer and analyzing.

When the condensation compound particle dispersion liquid of the invention is used as a releaser particle dispersion liquid in the manufacture of a toner, the average domain size of the releaser in the toner is preferably from 0.05 to 1.0 μm, and more preferably from 0.1 to 0.5 μm. When the domain size is in the above range, a releasing property is preferably improved in fixing.

The average domain size of a releaser in a toner can be measured according to a known method, for example, a method of confirming the cross sections of 50 toner particles with a transmission electron microscope (TEM) and taking the average is exemplified.

When the condensation compound particle dispersion liquid of the invention is used as a releaser particle dispersion liquid in the manufacture of a toner, transmittance (HAZE value) in a fixed image is excellent, so that preferred.

The transmittance (HAZE value) can be measured by a known method, e.g., according to the following method.

With the toner or developer obtained by using the condensation compound particle dispersion liquid of the invention as a releaser particle dispersion liquid in the manufacture of the toner, the toner weight per a unit area is adjusted to 18.0 mg/cm² with modified machine of Docu Centre Color 500 (constituents of fixing apparatus: heat roller and belt, nip width: 16 mm), a toner image of 3.5 mg/cm² is formed on OHP (XEROX FILM, manufactured by Fuji Xerox Office Supply), and fixing is carried out after adjusting fixing temperature to 180° C. and process speed to 180 mm/sec. The transmittance (HAZE value) of the obtained fixed image is found with a haze meter (direct reading type haze computer HGM-2DP, manufactured by Suga Test Instruments Co., Ltd.).

The HAZE value is preferably 35% or less, more preferably 30% or less, and still more preferably 25% or less. When the HAZE value is in the above range, it is thought that the fixed image has sufficiently practicable level of transmittance, and so preferred.

Electrostatic Image Developer:

The electrostatic image developing toner of the invention can be used as an electrostatic image developer. The developer is not particularly restricted besides containing the electrostatic image developing toner, and arbitrary composition of components can be taken according to purpose. When the electrostatic image developing toner is used alone, the developer is prepared as one component system electrostatic image developer, and when used in combination with a carrier, prepared as two component system electrostatic image developer.

As one component system developer, a method of forming a charged toner by triboelectrification with a developing sleeve or an electrification member, and developing in accordance with the latent image can also be applied.

The carrier is not especially restricted, but generally magnetic particles, e.g., iron powder, ferrite, iron oxide powder, nickel, etc.; resin covered carriers including magnetic particles as the core materials and covering the surfaces of the magnetic particles with resins, e.g., styrene resins, vinyl resins, ethylene resins, rosin resins, polyester resins, melamine resins, etc., or waxes, e.g., stearic acid, to form resin covering layers; and magnetic particle dispersed type carriers including magnetic particles dispersed in a binder resin are exemplified. Of these carriers, resin covered carriers are particularly preferred, since the electrification property of the toner and the resistance of the carrier at large can be controlled by the constitution of the resin covering layers.

The blending ratio of the toner of the invention and the carrier in two component system electrostatic image developer is generally from 2 to 10 weight parts of the toner per 100 weight parts of the carrier. The manufacturing method of the developer is not especially restricted, e.g., a method of blending with a V blender and the like can be exemplified.

Image-Forming Method:

The electrostatic image developing toner and the electrostatic image developer of the invention can be used in an image-forming method of ordinary electrostatic image developing system (an electrophotographic system).

The image-forming method of the invention is an image forming method including a latent image-forming process of forming an electrostatic latent image on the surface of a latent image holder, a developing process of forming a toner image by developing the electrostatic latent image formed on the surface of the latent image holder with a developer containing a toner, a transfer process of transferring the toner image formed on the surface of the latent image holder to the surface of a substance to be transferred, and a fixing process of thermally fixing the toner image transferred to the surface of the substance to be transferred, wherein the electrostatic image developing toner of the invention is used as the toner, or the electrostatic image developer of the invention is used as the developer.

Processes conventionally known in image-forming method can be used in each of the above processes, and these processes are disclosed, e.g., in JP-A-56-40868 and JP-A-49-91231.

The image-forming method of the invention may contain processes other than the processes described above, for example, a cleaning process of removing the electrostatic image developer remaining on the electrostatic latent image holder is preferably exemplified. In the image-forming method of the invention, an embodiment further including a recycling process is preferred. The recycling process is a process of transferring the electrostatic image developer recycled in the prior cleaning process to the developer layer. The image forming method of the embodiment including the recycling process can be used in image-forming apparatus such as copiers of a toner recycling system and facsimile terminal equipments. The image forming method including the recycling process can also be applied to a recycling system of an embodiment of omitting the cleaning process and recovering a toner simultaneously with a developer.

As the latent image holder, e.g., electrophotographic photoconductors and dielectric recording substances can be used.

In the case of an electrophotographic photoconductor, the surface of the electrophotographic photoconductor is uniformly charged with a Corotron charger or a contact charger, exposed, and then an electrostatic latent image is formed (the latent image-forming process). Subsequently, the latent image is brought into contact with or in close vicinity to a developing roll having a developer layer on the surface, the toner particles are adhered to the electrostatic latent image to form a toner image on the electrophotographic photoconductor (the developing process). The toner image formed is transferred to the surface of a substance to be transferred such as paper by utilizing a Corotron charger and the like (the transfer process). Further, the toner image transferred to the surface of the substance to be transferred is thermally fixed with a fixing apparatus (the fixing process), whereby a final toner image is formed.

Incidentally, in the thermal fixing with a fixing apparatus, a releaser is generally supplied to the fixing member in the fixing apparatus for the purpose of prevention of offset.

EXAMPLE

The invention will be described specifically with reference to examples, but the invention is by no means restricted thereto. In the following description, "parts" means "weight parts" unless otherwise indicated.

1) Condensation Reaction in Water

Example 1

| | |
|---|---|
| 3-Fluoro-4-dodecylbenzenesulfonic acid | 1.30 weight parts |
| Ion exchange water | 200 weight parts |
| Palmitic acid | 47 weight parts |
| Pentaerythritol | 6.5 weight parts |

The above components were mixed and melted by heating at 90° C., put in an aqueous solution and emulsified for 5 minutes with a homogenizer (ULTRA-TURRAX, manufactured by IKA). After further emulsification in an ultrasonic wave bath for 5 minutes, the emulsified product was retained at 70° C. in a flask for 15 hours with stirring. Thus, condensation compound particle dispersion liquid (1) having a median size of the particles of 280 nm, standard deviation of 0.19, and a melting point of 71° C. was obtained.

After termination of reaction, the reactor was soaked in ice water, particles were observed with SEM after freeze drying, and shape factor SF2 was measured. In the measurement, an optical microphotographic image of 5,000 magnifications was taken into image analyzer (LUZEX III, manufactured by NIRECO CORPORATION), and an image-analyzing program was used.

At least 500 particles were measured according to the following expression.

$$SF2 = \frac{L^2}{A} \times \frac{1}{4\pi} \times 100$$

wherein L represents the circumferential length of a latex particle, and A represents the surface area of a latex particle.

When a particle is complete round, SF2 is 100, and in the case of a pulverized particle, SF2 is generally 150 or so. It can be considered that the nearer the SF2 to 100, the more stable is the latex particle and free from bonding by fusion and heteromorphism of particle.

SF2 of the above condensation compound particles was 110, and the particles had stable particle shape.

Comparative Example 1

| | |
|---|---|
| 4-n-Dodecylbenzenesulfonic acid (straight-chain DBSA) | 1.20 weight parts |
| Ion exchange water | 200 weight parts |
| Palmitic acid | 47 weight parts |
| Pentaerythritol | 6.5 weight parts |

Particles were manufactured with the above components in the same manner as in Example 1, and condensation compound particle dispersion liquid (2) having a median size of the particles of 350 nm, standard deviation of 0.33, and a melting point of 71° C. was obtained. SF2 was 140 and fusion bonding of particles was observed.

TABLE 1

| | Example 1 | Comparative Example 1 |
|---|---|---|
| Catalyst | 3-Fluoro-4-dodecylbenzene-sulfonic acid | Straight-chain DBSA |
| Median size of particles (nm) | 280 | 350 |
| Standard deviation | 0.19 | 0.33 |
| Melting point (° C.) | 71 | 71 |
| SF2 | 110 | 140 (flocculation was observed) |

2) Polyondensation Reaction in Water

Example 2

Water Phase

| | |
|---|---|
| 3-Fluoro-4-dodecylbenzenesulfonic acid | 1.3 weight parts |
| Ion exchange water | 200 weight parts |

Oil Phase:

| | |
|---|---|
| 1,9-Nonanediol | 16.0 weight parts |
| Dodecanoic diacid | 23.0 weight parts |
| Styrene | 5.0 weight parts |

The above water phase was mixed and dissolved in a constant temperature bath at 70° C. On the other hand, the oil phase was mixed and melted by heating at 120° C., and then put into the above water phase and emulsified at 8,000 rpm for 5 minutes with a homogenizer (ULTRA-TURRAX, manufactured by IKA). After further emulsification in an ultrasonic wave bath for 5 minutes, the emulsified product was put in a reactor equipped with a stirrer, and subjected to polycondensation under nitrogen atmosphere at 70° C. for 24 hours.

To the resin particle dispersion liquid was added an aqueous solution obtained by dissolving 0.3 weight parts of ammonium persulfate to 5 weight parts of ion exchange water, and polymerization was carried out under nitrogen atmosphere for further 6 hours.

Thus, polyester resin particle dispersion liquid (1) having a median size of the particles of 310 nm, standard deviation of 0.25, a melting point of 57° C., and weight-average molecular weight of 4,700 was obtained. The obtained particles were dried in the same manner as in Example 1, and SF2 measured was 115.

Comparative Example 2

Water Phase

| | |
|---|---|
| Dodecylbenzenesulfonic acid (DBSA, Hard type, Tayca Power B120, manufactured by TAYCA CORPORATION) | 1.20 weight parts |
| Ion exchange water | 200 weight parts |

Oil Phase:

| | |
|---|---|
| 1,9-Nonanediol | 16.0 weight parts |
| Dodecanoic diacid | 23.0 weight parts |
| Styrene | 5.0 weight parts |

Polycondensation particles were manufactured with the above materials in the same manner as in Example 2, and polyester resin particle dispersion liquid (2) having a median size of the particles of 380 nm, standard deviation of 0.43, a melting point of 56° C., and weight-average molecular weight of 2,900 was obtained. The obtained particles were dried in the same manner as in Example 1, and SF2 measured was 135, and heteromorphism of particles due to fusion bonding was observed.

TABLE 2

| | Example 2 | Comparative Example 2 |
|---|---|---|
| Catalyst | 3-Fluoro-4-dodecylbenzene-sulfonic acid | DBSA (Hard type) |
| Weight-average molecular weight | 4,700 | 2,900 |
| Median size of particles (nm) | 310 | 380 |

TABLE 2-continued

|  | Example 2 | Comparative Example 2 |
|---|---|---|
| Standard deviation | 0.25 | 0.43 |
| Melting point (° C.) | 57 | 56 |
| SF2 | 115 | 135 (flocculation was observed) |

3) Direct Thioesterification Reaction (Bulk)

Example 3

| Lauric acid | 20 weight parts |
|---|---|
| Dodecanethiol | 20.5 weight parts |
| 3-Fluoro-4-dodecylbenzenesulfonic acid | 0.25 weight parts (0.7 mol %) |

The above materials were mixed and put in a reactor equipped with a stirrer, and thioesterification reaction was carried out at 120° C. for 24 hours. A homogeneous reaction product was obtained. The obtained compound was subjected to proton NMR measurement, and the yield computed from the comparison of the peak area of the carboxyl group or thiol group with the peak area of the thioester group was 91%.

Comparative Example 3

| Lauric acid | 20 weight parts |
|---|---|
| Dodecanethiol | 20.5 weight parts |
| Pentadecylbenzenesulfonic acid (PDBSA, Hard type, Tayca Power B150, manufactured by TAYCA CORPORATION) | 0.26 weight parts (0.7 mol %) |

The above materials were mixed and put in a reactor equipped with a stirrer, and thioesterification reaction was carried out at 120° C. for 24 hours. A homogeneous reaction product was obtained. The obtained compound was subjected to proton NMR measurement, and the yield computed from the comparison of the peak area of the carboxyl group or thiol group with the peak area of the thioester group was 62%.

TABLE 3

|  | Example 3 | Comparative Example 3 |
|---|---|---|
| Catalyst | 3-Fluoro-4-dodecylbenzene-sulfonic acid | PDBSA (Hard type) |
| Yield (%) | 91 | 62 |

4) Polycondensation of Amorphous Resin (Bulk)

Example 4

| Cyclohexanedicarboxylic acid | 17.0 weight parts |
|---|---|
| Ethylene oxide 2 mol adduct of Bisphenol A | 16.0 weight parts (50 mol %) |
| Ethylene oxide 2 mol adduct of Bisphenol S | 17.0 weight parts (50 mol %) |
| 3-Fluoro-4-pentadecylbenzene-sulfonic acid | 0.08 weight parts (0.1 mol %) |

The above materials were mixed and put in a reactor equipped with a stirrer, and polycondensation reaction was carried out at 120° C. for 24 hours. A homogeneous and transparent, milky white amorphous polyester resin was obtained.

Weight-average molecular weight by GPC: 14,500
Number-average molecular weight by GPC: 4,050
Tg (onset $2^{nd}$): 64.3° C.

The thus-obtained resin was put in a three-neck flask equipped with a stirrer and a cooling pipe, and stirring was continued with gradually adding a 1N NaOH aqueous solution while maintaining the temperature at 95° C. When the NaOH aqueous solution in total of 50 weight parts was added, the resin showed a slurry state. The slurry was put in a flask containing 180 weight parts of ion exchange water adjusted to 85° C., emulsified with homogenizer (ULTRA-TURRAX, manufactured by IKA) for 10 minutes, further emulsified by 10 passes with a super high pressure homogenizer (Nanomizer, manufactured by YOSHIDA KIKAI CO., LTD.), and then the dispersion liquid was cooled with ice, whereby polyester resin particle dispersion liquid (3) was obtained. The median size of the resin particles was 190 nm and the standard deviation was 0.24.

Comparative Example 4

| Cyclohexanedicarboxylic acid | 17.0 weight parts |
|---|---|
| Ethylene oxide 2 mol adduct of Bisphenol A | 16.0 weight parts (50 mol %) |
| Ethylene oxide 2 mol adduct of Bisphenol S | 17.0 weight parts (50 mol %) |
| 4-n-Dodecylbenzenesulfonic acid | 0.07 weight parts (0.1 mol %) |

The above materials were mixed and put in a reactor equipped with a stirrer, and polycondensation reaction was carried out at 120° C. for 24 hours. A homogeneous and transparent, pale yellow amorphous polyester resin was obtained.

Weight-average molecular weight by GPC: 8,700
Number-average molecular weight by GPC: 3,300
Tg (onset $2^{nd}$): 59.5° C.

Polyester resin particle dispersion liquid (4) was manufactured in the same manner as in Example 4. The median size of the resin particles was 180 nm and the standard deviation was 0.46.

Comparative Example 5

| Cyclohexanedicarboxylic acid | 17.0 weight parts |
|---|---|
| Ethylene oxide 2 mol adduct of Bisphenol A | 16.0 weight parts (50 mol %) |
| Ethylene oxide 2 mol adduct of Bisphenol S | 17.0 weight parts (50 mol %) |
| 4-n-Dodecylbenzenesulfonic acid | 0.15 weight parts (0.2 mol %) |

The above materials were mixed and put in a reactor equipped with a stirrer, and polycondensation reaction was carried out at 120° C. for 24 hours. A homogeneous and transparent, pale yellow amorphous polyester resin was obtained.
Weight-average molecular weight by GPC: 11,500
Number-average molecular weight by GPC: 3,880
Tg (onset $2^{nd}$): 62.0° C.

Polyester resin particle dispersion liquid (5) was manufactured in the same manner as in Example 4. The median size of the resin particles was 180 nm and the standard deviation was 0.30.

TABLE 4

|  | Example 4 | Comparative Example 4 | Comparative Example 5 |
|---|---|---|---|
| Catalyst | 3-Fluoro-4-pentadecyl-benzenesulfonic acid | 4-n-Dodecyl-benzenesulfonic acid | 4-n-Dodecyl-benzenesulfonic acid |
| Weight-average molecular weight | 14,500 | 8,700 | 11,500 |
| Glass transition point (° C.) | 64.3 | 59.5 | 62.0 |
| Coloration | Milky white | Pale yellow | Pale yellow |
| Median size (nm) | 190 | 180 | 180 |
| Standard deviation | 0.24 | 0.46 | 0.30 |

5) Manufacture of Toner

Preparation of Releaser Particle Dispersion Liquid (W1)

| | |
|---|---|
| Polyethylene wax (Polywax 725, melting point: 103° C., manufactured by BAKER PETROLITE) | 30 weight parts |
| Cationic surfactant (SANISOL B50, manufactured by Kao Corporation) | 3 weight parts |
| Ion exchange water | 67 weight parts |

The above components were thoroughly dispersed with a homogenizer (ULTRA-TURRAX, manufactured by IKA) while heating at 95° C., and then subjected to dispersing treatment with a pressure discharge type homogenizer (Gaulin Homogenizer, manufactured by Gaulin) to obtain releaser particle dispersion liquid (W1). The number-average particle size $D_{50n}$ of the releaser particles in the obtained dispersion liquid was 460 nm. After that, ion exchange water was added to adjust the solid content concentration of the dispersion liquid to 30%.

Preparation of Cyan Pigment Dispersion Liquid

| | |
|---|---|
| Cyan pigment (C.I. Pigment Blue 15:3, manufactured by Dainichiseika Color & Chemicals Mfg. Co., Ltd.) | 20 weight parts |
| Anionic surfactant (Neogen SC, manufactured by DAI-ICHI KOGYO SEIYAKU CO., LTD.) | 2 weight parts |
| Ion exchange water | 78 weight parts |

The above components were mixed and dissolved, and then dispersed with a homogenizer (ULTRA-TURRAX, manufactured by IKA) for 5 minutes and then in an ultrasonic wave bath for 10 minutes, whereby a cyan pigment dispersion liquid was obtained. The number-average particle size $D_{50n}$ of the pigment in the obtained dispersion liquid was 120 nm. After that, ion exchange water was added to adjust the solid content concentration of the dispersion liquid to 20%.

Preparation of Resin Particle Dispersion Liquid A: Amorphous Vinyl Resin Latex

| | |
|---|---|
| Styrene | 460 weight parts |
| n-Butyl acrylate | 140 weight parts |
| Acrylic acid | 12 weight parts |
| Dodecanethiol | 9 weight parts |

The above components were mixed and dissolved to prepare a solution.

On the other hand, 12 weight parts of anionic surfactant (DOWFAX, manufactured by Dow Chemical Company) was dissolved in 250 weight parts of ion exchange water, to which the above solution was added and dispersion liquid emulsified in a flask (monomer emulsified liquid A).

Further, 1 weight part of anionic surfactant (DOWFAX, manufactured by Dow Chemical Company) was dissolved in 555 weight parts of ion exchange water, and put in a flask for polymerization.

The flask for polymerization was sealed, a reflux tube was attached to the flask and, with stirring slowly, the flask was heated to 75° C. in a water bath, and retained.

Ammonium persulfate (9 weight parts) was dissolved in 43 weight parts of ion exchange water, and the solution was dropped into the polymerization flask via a quantitative pump over 20 minutes, and then monomer emulsified liquid A was also dropped via a quantitative pump over 200 minutes.

While continuing stirring slowly, the polymerization flask was maintained at 75° C. for 3 hours, and polymerization was terminated.

Thus, anionic resin particle dispersion liquid A having a median size of the particles of 290 nm, glass transition point of 52.0° C., weight-average molecular weight of 30,000, and solids content of 42% was obtained.

Toner Example 1

Toner Using Condensation Compound Example 1

Manufacture of Cyan Toner (Toner C1):

| | |
|---|---|
| Condensation compound particle dispersion liquid (1) | 50 weight parts |
| Resin particle dispersion liquid A | 90 weight parts |
| Cyan pigment dispersion liquid (C1) | 60 weight parts |
| 10 wt % Aqueous solution of polyalminum chloride (PAC1000W, manufactured by Asada Chemical Industry Co., Ltd.) | 15 weight parts |
| 1% Nitric acid aqueous solution | 3 weight parts |

After the above components were dispersed in a rounded stainless steel flask with a homogenizer (ULTRA-TURRAX, manufactured by IKA) at 5,000 rpm for 3 minutes, the flask was covered with a cap equipped with a stirrer having a magnetic seal, a thermometer and a pH meter. A mantel heater for heating was set and the reaction solution was heated to 62°

C. at a rate of 1° C./min by arbitrarily adjusting the rotation number of stirring of the entire dispersion liquid in the flask to the minimum, the reaction solution was retained at 62° C. for 30 minutes, and the particle sizes of the aggregated particles were confirmed with a coulter counter (TAII, manufactured by Nikkaki-Bios). Immediately after stopping temperature increase, 50 weight parts of resin particle dispersion liquid (L1) was added, retained for 30 minutes, a sodium hydroxide aqueous solution was added until the pH in the system reached 6.5, and then the reaction system was heated at a rate of 1° C./min to 97° C. After temperature increase, a nitric acid aqueous solution was added to the system to adjust the pH of the system to 5.0, and the system was retained for 10 hours to melt the aggregated particles by heat. The temperature in the system was lowered to 50° C., a sodium hydroxide aqueous solution was added to adjust the pH to 12.0, and the reaction solution was retained for 10 minutes. After that, the reaction solution was taken out of the flask, sufficiently filtered with ion exchange water, washed by passing water, further dispersed in ion exchange water so that the solids content became 10 wt %, nitric acid was added and the reaction system was stirred at pH 3.0 to 10 minutes. After that, the system was again thoroughly filtered with ion exchange water, washed by passing water, and the obtained slurry was frozen dried to thereby obtain a cyan toner (toner C1). The thus-manufactured toner had cumulative volume-average particle size $D_{50}$ of 5.7 μm, volume-average particle size distribution index GSDv of 1.23, and shape factor of the toner particles was 128.

Further, as a result of confirming the cross sections of 50 toner particles with a transmission electron microscope (TEM), the average domain size of the releaser was 0.7 μm.

The cumulative volume-average particle size $D_{50}$ and the volume-average particle size distribution index GSDv of the toner were found with a laser diffraction type particle size distribution measuring apparatus (LA-700, manufactured by Horiba, Ltd.), and the shape factor was found by observation of the shapes with a Ruzex image analyzer.

To the cyan toner, silica ($SiO_2$) fine particles having an average primary particle size of 40 nm subjected to surface hydrophobitization treatment with hexamethyldisilazane (hereinafter sometimes referred to as "HMDS"), and fine particles of metatitanic acid compound having an average primary particle size of 20 nm that was a reaction product of metatitanic acid and isobutyltrimethoxysilane were added respectively in an amount of 1 wt %, and the mixture was admixed with a Henschel mixer, whereby cyan outer additive toner was manufactured.

In the next place, each 5 weight parts of these toners, and 100 weight parts of ferrite particles (an average particle size: 35 μm) resin-covered with methyl polymethacrylate (Mw: 78,000) in an amount of 1.5 wt % to the weight of the carrier were mixed to prepare a two-component developer.

By using the obtained developer, with modified machine of Docu Centre Color 500 (constituents of fixing apparatus: heat roller and belt, nip width: 16 mm), a toner image of 3.5 mg/cm² was formed on OHP (XEROX FILM, manufactured by Fuji Xerox Office Supply), and fixing was carried out after adjusting fixing temperature to 180° C. and process speed to 60 mm/sec. The transmittance (HAZE value) of the obtained fixed image was found with a haze meter (direct reading type haze computer HGM-2DP, manufactured by Suga Test Instruments Co., Ltd.). In general, when the HAZE value is 35% or less, it is thought that the fixed image has sufficiently practicable level of transmittance. The transmittance of the developer is 24%, which means that dispersing state of the releaser is good.

Toner Comparative Example 1

Toner Using Condensation Compound Comparative Example 1

A toner was manufactured in the same manner as in Toner Example 1 except for using condensation compound particles (2) in place of condensation compound particles (1). The thus-manufactured toner had cumulative volume-average particle size $D_{50}$ of 5.8 μm, volume-average particle size distribution index GSDv of 1.24, and shape factor of the toner particles was 129. The domain size of the releaser by observation with TEM was 1.8 μm, and the image HAZE value found according to the same manner as in Toner Example 1 was 42%, and it is apparent that the transmittance is deteriorated.

TABLE 5

|  | Toner Example 1 | Toner Comparative Example 1 |
| --- | --- | --- |
| Condensation compound used | Example 1 | Comparative Example 1 |
| $D_{50}$ (μm) | 5.7 | 5.8 |
| GSDv | 1.23 | 1.24 |
| SF1 | 128 | 129 |
| Releaser domain size (μm) | 0.7 | 1.8 |
| HAZE value | 24 | 42 |

Toner Example 2

Toner Using Polyester Resin Particle Dispersion Liquid (1)

| | |
| --- | --- |
| Polyester resin particle dispersion liquid (1) | 100 weight parts |
| Resin particle dispersion liquid A | 60 weight parts |
| Releaser particle dispersion liquid (W1) | 33 weight parts |
| Cyan pigment dispersion liquid | 60 weight parts |
| 10 wt % Aqueous solution of polyalminum chloride (PAC1000W, manufactured by Asada Chemical Industry Co., Ltd.) | 15 weight parts |
| 1% Nitric acid aqueous solution | 3 weight parts |

A toner was manufactured by using the above materials in the same manner as in Toner Example 1. The thus-manufactured toner had cumulative volume-average particle size $D_{50}$ of 5.8 μm, volume-average particle size distribution index GSDv of 1.24, and shape factor of the toner particles was 127.

Toner Comparative Example 2

Toner Using Polyester Resin Particle Dispersion Liquid (2)

A toner in Toner Comparative Example 2 was manufactured in the same manner as in Toner Example 2 except for using polyester resin particle dispersion liquid (2) in place of (1). The thus-manufactured toner had cumulative volume-average particle size $D_{50}$ of 6.0 µm, volume-average particle size distribution index GSDv of 1.26, and shape factor of the toner particles was 125.

Toner Example 3

Toner Using Polyester Resin Particle Dispersion Liquid (3)

| | |
|---|---|
| Polyester resin particle dispersion liquid (3) | 120 weight parts |
| Resin particle dispersion liquid A | 40 weight parts |
| Releaser particle dispersion liquid (W1) | 33 weight parts |
| Cyan pigment dispersion liquid | 60 weight parts |
| 10 wt % Aqueous solution of polyaluminum chloride (PAC1000W, manufactured by Asada Chemical Industry Co., Ltd.) | 15 weight parts |
| 1% Nitric acid aqueous solution | 3 weight parts |

A toner was manufactured by using the above materials in the same manner as in Toner Example 1. The thus-manufactured toner had cumulative volume-average particle size $D_{50}$ of 5.8 µm, volume-average particle size distribution index GSDv of 1.22, and shape factor of the toner particles was 129.

Toner Comparative Example 3

Toner Using Polyester Resin Particle Dispersion Liquid (4)

A toner in Toner Comparative Example 2 was manufactured in the same manner as in Toner Example 3 except for using polyester resin particle dispersion liquid (4) in place of (3). The thus-manufactured toner had cumulative volume-average particle size $D_{50}$ of 5.9 µm, volume-average particle size distribution index GSDv of 1.26, and shape factor of the toner particles was 128.

Toner Comparative Example 4

Toner Using Polyester Resin Particle Dispersion Liquid (5)

A toner in Toner Comparative Example 2 was manufactured in the same manner as in Toner Example 3 except for using polyester resin particle dispersion liquid (5) in place of (3). The thus-manufactured toner had cumulative volume-average particle size $D_{50}$ of 5.9 µm, volume-average particle size distribution index GSDv of 1.24, and shape factor of the toner particles was 128.

Evaluation of Charge Stability and Image Quality:

The developers in Toner Examples 2 and 3 and Comparative Examples 2 to 4 were subjected to continuous running test of 30,000 sheets with modified machine of Docu Centre Color 500 (manufactured by Fuji Xerox Office Supply). The charge characteristics of toner at initial stage and after continuous running of 30,000 sheets were measured according to a blowing off method (Toshiba Chemical Co., Ltd., TB200, the weight of the toner to the developer: 5%, blowing gas: air, blowing pressure: 1.0 kg/cm$^2$, blowing time: 30 seconds).

Soiling of the background was visually evaluated of the image quality at initial stage and after continuous running of 30,000 sheets.

Fixing Strength:

Evaluation of fixing strength was performed according to the following method. Unfixed solid sample was formed on ecolor 081 A-4 size paper (manufactured by. Fuji Xerox Office Supply) with modified machine of Docu Centre Color 500 (manufactured by Fuji Xerox Office Supply). The weight of the toner per the unit area in the solid sample was adjusted to from 0.7 to 0.8 mg/cm$^2$. After the manufactured fixed sample was folded in half, a roll (outer diameter: 600 mm, made of brass) having load of 500 g or so was rolled on the crease at a constant speed, the crease of the fixed image was rubbed with a waste, and the state of falling off of the image was observed.

Evaluation was performed by sensory evaluation according to the following criteria.

A: A crease is seen but the image is not missing, or little if any.
B: A slight white crease is seen and the image is partly missing.
C: A white belt-like crease is conspicuous and more than half of the image is missing.

TABLE 6

| | Toner Example 2 | Toner Comparative Example 2 | Toner Example 3 | Toner Comparative Example 3 | Toner Comparative Example 4 |
|---|---|---|---|---|---|
| Polyester particle dispersion liquid used | (1) | (2) | (3) | (4) | (4) |
| D50 (µm) | 5.8 | 6.0 | 5.8 | 5.9 | 5.9 |
| GSDv | 1.24 | 1.26 | 1.22 | 1.26 | 1.25 |
| SF1 | 127 | 125 | 129 | 128 | 128 |
| Initial electrification (µC/g) | −38.5 | −39.1 | −34.1 | −36.2 | −40.6 |
| Electrification after 30,000 sheets of running test (µC/g) | −29.2 | −15.2 | −29.8 | −19.5 | −7.9 |
| Initial image quality | Good | Good | Good | Good | Good |
| Image quality after 30,000 sheets of running test | Good | Background is soiled. | Good | Background is soiled. | Soiling of background is conspicuous. |
| Image strength | A | C | A | C | B |

Example 5

Condensation compound particle dispersion liquid (6) was obtained in the same manner as in the condensation reaction in water in Example 1 except for using 2-fluoro-4-dodecylbenzenesulfonic acid in place of 3-fluoro-4-dodecylbenzenesulfonic acid. The obtained condensation compound particle dispersion liquid (6) was excellent in median size and standard deviation, and was free from bonding by fusion of particles and heteromorphism of particles.

Further, a toner was manufactured in the same manner as in Toner Example 1 except for using condensation compound particle dispersion liquid (6) in place of condensation compound particle dispersion liquid (1). The obtained toner was excellent in HAZE value.

Further, polyester resin particle dispersion liquid (6) was obtained in the same manner as in polyondensation reaction in water in Example 2 except for using 2-fluoro-4-dodecylbenzenesulfonic acid in place of 3-fluoro-4-dodecylbenzenesulfonic acid. The obtained polyester resin particle dispersion liquid (6) was excellent in weight-average molecular weight, median size and standard deviation, and was free from bonding by fusion of particles and heteromorphism of particles.

Further, a toner was manufactured in the same manner as in Toner Example 2 except for using polyester resin particle dispersion liquid (6) in place of polyester resin particle dispersion liquid (1). The obtained toner was excellent in charge stability evaluation, image quality evaluation and image strength.

Further, when direct thioesterification reaction was performed in the same manner as in Example 3 except for using 2-fluoro-4-dodecylbenzenesulfonic acid in place of 3-fluoro-4-dodecylbenzenesulfonic acid, thioesterification proceeded in high yield.

Example 6

Condensation compound particle dispersion liquid (7) was obtained in the same manner as in the condensation reaction in water in Example 1 except for using 3,5-difluoro-4-dodecyl-benzenesulfonic acid in place of 3-fluoro-4-dodecylbenzene-sulfonic acid. The obtained condensation compound particle dispersion liquid (7) was excellent in median size and standard deviation, and was free from bonding by fusion of particles and heteromorphism of particles.

Further, a toner was manufactured in the same manner as in Toner Example 1 except for using condensation compound particle dispersion liquid (7) in place of condensation compound particle dispersion liquid (1). The obtained toner was excellent in HAZE value.

Further, polyester resin particle dispersion liquid (7) was obtained in the same manner as in polyondensation reaction in water in Example 2 except for using 3,5-difluoro-4-dodecyl-benzenesulfonic acid in place of 3-fluoro-4-dodecylbenzene-sulfonic acid. The obtained polyester resin particle dispersion liquid (7) was excellent in weight-average molecular weight, median size and standard deviation, and was free from bonding by fusion of particles and heteromorphism of particles.

Further, a toner was manufactured in the same manner as in Toner Example 2 except for using polyester resin particle dispersion liquid (7) in place of polyester resin particle dispersion liquid (1). The obtained toner was excellent in charge stability evaluation, image quality evaluation and image strength.

Further, when direct thioesterification reaction was performed in the same manner as in Example 3 except for using 3,5-difluoro-4-dodecylbenzenesulfonic acid in place of 3-fluoro-4-dodecylbenzenesulfonic acid, thioesterification proceeded in high yield.

Comparative Example 6

Condensation compound particle dispersion liquid (8) was obtained in the same manner as in the condensation reaction in water in Example 1 except for using 2-fluoro-4-heptyl-benzenesulfonic acid in place of 3-fluoro-4-dodecylbenzene-sulfonic acid. The obtained condensation compound particle dispersion liquid (8) was inferior to Examples 1, 5 and 6 in median size and standard deviation, and bonding by fusion of particles and heteromorphism of particles were observed.

Further, a toner was manufactured in the same manner as in Toner Example 1 except for using condensation compound particle dispersion liquid (8) in place of condensation compound particle dispersion liquid (1). The obtained toner was inferior to Examples 1, 5 and 6 in HAZE value.

Further, polyester resin particle dispersion liquid (8) was obtained in the same manner as in polyondensation reaction in water in Example 2 except for using 2-fluoro-4-heptylbenzene-sulfonic acid in place of 3-fluoro-4-dodecylbenzene-sulfonic acid. The obtained polyester resin particle dispersion liquid (8) was inferior to Examples 1, 5 and 6 in weight-average molecular weight, median size and standard deviation, and bonding by fusion of particles and heteromorphism of particles were observed.

Further, a toner was manufactured in the same manner as in Toner Example 2 except for using polyester resin particle dispersion liquid (8) in place of polyester resin particle dispersion liquid (2). The obtained toner was inferior to Examples 2, 5 and 6 in charge stability evaluation, image quality evaluation and image strength.

Further, when direct thioesterification reaction was performed in the same manner as in Example 3 except for using 2-fluoro-4-heptylbenzenesulfonic acid in place of 3-fluoro-4-dodecylbenzenesulfonic acid, the yield was inferior to Examples 1, 5 and 6.

Comparative Example 7

Condensation compound particle dispersion liquid (9) was obtained in the same manner as in the condensation reaction in water in Example 1 except for using 2-fluoro-4-docosyl-benzenesulfonic acid in place of 3-fluoro-4-dodecylbenzene-sulfonic acid. The obtained condensation compound particle dispersion liquid (9) was inferior to Examples 1, 5 and 6 in median size and standard deviation, and bonding by fusion of particles and heteromorphism of particles were observed.

Further, a toner was manufactured in the same manner as in Toner Example 1 except for using condensation compound particle dispersion liquid (9) in place of condensation compound particle dispersion liquid (1). The obtained toner was inferior to Examples 1, 5 and 6 in HAZE value.

Further, polyester resin particle dispersion liquid (9) was obtained in the same manner as in polyondensation reaction in water in Example 2 except for using 2-fluoro-4-docosyl-benzene-sulfonic acid in place of 3-fluoro-4-dodecylbenze-nesulfonic acid. The obtained polyester resin particle dispersion liquid (9) was inferior to Examples 1, 5 and 6 in weight-average molecular weight, median size and standard deviation, and bonding by fusion of particles and heteromorphism of particles were observed.

Further, a toner was manufactured in the same manner as in Toner Example 2 except for using polyester resin particle dispersion liquid (9) in place of polyester resin particle dispersion liquid (2). The obtained toner was inferior to Examples 2, 5 and 6 in charge stability evaluation, image quality evaluation and image strength.

Further, when direct thioesterification reaction was performed in the same manner as in Example 3 except for using 2-fluoro-4-docosylbenzenesulfonic acid in place of 3-fluoro-4-dodecylbenzenesulfonic acid, the yield was inferior to Examples 1, 5 and 6.

The results of evaluations of the toners in Examples 5 and 6 and Comparative Examples 6 and 7 are shown in Table 7 below.

TABLE 7

| | Toner Example | | | |
|---|---|---|---|---|
| | Example 5 | Example 6 | Comparative Example 6 | Comparative Example 7 |
| polyester particle dispersion liquid Used | (6) | (7) | (8) | (9) |
| $D_{50}$ (μm) | 5.7 | 5.5 | 7.1 | 7.9 |
| GSDv | 1.22 | 1.23 | 1.33 | 1.38 |
| SF1 | 127 | 129 | 133 | 136 |
| Initial electrification (μC/g) | −35.1 | −30.9 | −19.9 | −20.5 |
| Electrification after 30,000 sheets of running test (μC/g) | −34.9 | −29.8 | −10.1 | −9.9 |
| Initial image quality | Good | Good | Good | Good |
| Image quality after 30,000 sheets of running test | Good | Good | Background is soiled. | Background is soiled. |
| Image strength | A | A | C | C |

What is claimed is:

1. A dispersion liquid of condensation compound particles, comprising:
a dispersion medium; and
particles containing a condensation compound dispersed in the dispersion medium,
wherein the condensation compound is a condensation compound manufactured by a manufacturing method of a condensation compound, comprising:
condensing a condensable composition with a Bronsted acid compound represented by formula (I) as a catalyst;

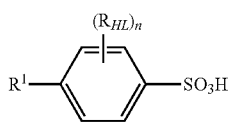

(I)

wherein n represents an integer of from 1 to 2;
$R_{HL}$('s) each independently represents Cl or F; and
$R^1$ represents an alkyl group having from 8 to 20 carbon atoms,
wherein the condensable composition comprises a polyhydric alcohol, and at least one of a polycarboxylic acid and a hydroxycarboxylic acid, wherein the Bronsted acid compound is selected from the group consisting of 2-fluoro-4-octylbenzenesulfonic acid, 3-fluoro-4-octylbenzenesulfonic acid, 2-fluoro-4-decylbenzenesulfonic acid, 3-fluoro-4-decylbenzenesulfonic acid, 2-fluoro-4-dodecylbenzenesulfonic acid, 3-fluoro-4-dodecylbenzenesulfonic acid, 2-fluoro-4-pentadecylbenzenesulfonic acid, 3-fluoro-4-pentadecylbenzenesulfonic acid, 2-fluoro-4-octadecylbenzenesulfonic acid, 3-fluoro-4-octadecylbenzenesulfonic acid, 2-chloro-4-octylbenzenesulfonic acid, 3-chloro-4-octylbenzenesulfonic acid, 2-chloro-4-decylbenzenesulfonic acid, 3-chloro-4-decylbenzenesulfonic acid, 2-chloro-4-dodecylbenzenesulfonic acid, 3-chloro-4-dodecylbenzenesulfonic acid, 2-chloro-4-pentadecylbenzenesulfonic acid, 3-chloro-4-pentadecylbenzenesulfonic acid, 2-chloro-4-octadecylbenzenesulfonic acid, 3-chloro-4-octadecylbenzenesulfonic acid, 3,5-difluoro-4-octylbenzenesulfonic acid, 3,5-dichloro-4-octylbenzenesulfonic acid, 3-chloro-5-fluoro-4-octylbenzenesulfonic acid, 3,5-difluoro-4-decylbenzenesulfonic acid, 3,5-dichloro-4-decylbenzenesulfonic acid, 3-chloro-5-fluoro-4-decylbenzenesulfonic acid, 3,5-difluoro-4-dodecylbenzenesulfonic acid, 3,5-dichloro-4-dodecylbenzenesulfonic acid, 3-chloro-5-fluoro-4-dodecylbenzenesulfonic acid, 3,5-difluoro-4-pentadecylbenzenesulfonic acid, 3,5-dichloro-4-pentadecylbenzenesulfonic acid, and 3-chloro-5-fluoro-4-pentadecylbenzenesulfonic acid.

2. A dispersion liquid of resin particles, comprising:
a dispersion medium; and
resin particles containing a binder resin dispersed in the dispersion medium,
wherein the binder resin is a binder resin manufactured by polycondensing a polycondensable monomer with a Bronsted acid represented by formula (I) as a catalyst;

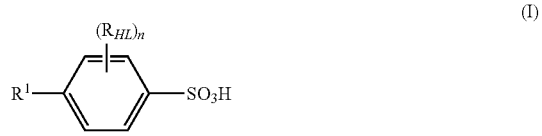

(I)

wherein n represents an integer of from 1 to 2;
$R_{HL}$('s) each independently represents Cl or F; and
$R^1$ represents an alkyl group having from 8 to 20 carbon atoms, wherein the polycondensable monomer comprises a polyhydric alcohol, and at least one of a polycarboxylic acid and a hydroxycarboxylic acid, wherein the Bronsted acid compound is selected from the group consisting of 2-fluoro-4-octylbenzenesulfonic acid, 3-fluoro-4-octylbenzenesulfonic acid, 2-fluoro-4-decylbenzenesulfonic acid, 3-fluoro-4-decylbenzenesulfonic acid, 2-fluoro-4-dodecylbenzenesulfonic acid, 3-fluoro-4-dodecylbenzenesulfonic acid, 2-fluoro-4-pentadecylbenzenesulfonic acid, 3-fluoro-4-pentadecylbenzenesulfonic acid, 2-fluoro-4-octadecylbenzenesulfonic acid, 3-fluoro-4-octadecylbenzenesulfonic acid, 2-chloro-4-octylbenzenesulfonic acid, 3-chloro-4-octylbenzenesulfonic acid, 2-chloro-4-decylbenzenesulfonic acid, 3-chloro-4-decylbenzenesulfonic acid, 2-chloro-4-dodecylbenzenesulfonic acid, 3-chloro-4-dodecylbenzenesulfonic acid, 2-chloro-4-pentadecylbenzenesulfonic acid, 3-chloro-4-pentadecylbenzenesulfonic acid, 2-chloro-4-octadecylbenzenesulfonic acid, 3-chloro-4-octadecylbenzenesulfonic acid, 3,5-difluoro-4-octylbenzenesulfonic acid, 3,5-dichloro-4-octylbenzenesulfonic acid, 3-chloro-5-fluoro-4-octylbenzenesulfonic acid, 3,5-difluoro-4-decylbenzenesulfonic acid, 3,5-dichloro-4-decylbenzenesulfonic acid, 3-chloro-5-fluoro-4-decylbenzenesulfonic acid, 3,5-difluoro-4-dodecylbenzenesulfonic acid, 3,5-dichloro-4-dodecylbenzenesulfonic acid, 3-chloro-5-fluoro-4-dodecylbenzenesulfonic acid, 3,5-difluoro-4-pentadecylbenzenesulfonic acid, 3,5-dichloro-4-pentadecylbenzenesulfonic acid, and 3-chloro-5-fluoro-4-pentadecylbenzenesulfonic acid.

3. The dispersion liquid of condensation compound particles according to claim 1, wherein n=1.

4. The dispersion liquid of condensation compound particles according to claim 1, wherein n=2.

5. The dispersion liquid of condensation compound particles according to claim 1, wherein the Bronsted acid compound is selected from the group consisting of 2-fluoro-4-n-octylbenzenesulfonic acid, 3-fluoro-4-n-octylbenzenesulfonic acid, 2-fluoro-4-n-dodecylbenzenesulfonic acid, 3-fluoro-4-n-dodecylbenzenesulfonic acid, 2-fluoro-4-n-pentadecylbenzenesulfonic acid, 3-fluoro-4-n-pentadecylbenzenesulfonic acid, 2-fluoro-4-n-octadecylbenzenesulfonic acid, 3-fluoro-4-n-octadecylbenzenesulfonic acid, and 3,5-difluoro-4-dodecylbenzenesulfonic acid.

6. The dispersion liquid of condensation compound particles according to claim 1, wherein the Bronsted acid compound is selected from the group consisting of 3-fluoro-4-n-dodecylbenzenesulfonic acid, 3-fluoro-4-n-pentadecylbenzenesulfonic acid and 3-fluoro-4-n-octadecylbenzenesulfonic acid.

* * * * *